United States Patent [19]

Hefner, Jr. et al.

[11] Patent Number: 5,248,740
[45] Date of Patent: Sep. 28, 1993

[54] BLENDS OF MESOGENIC POLYTHIIRANES AND EPOXY RESINS

[75] Inventors: Robert E. Hefner, Jr.; Jimmy D. Earls, both of Lake Jackson, Tex.

[73] Assignee: The Dow Chemical Company, Midland, Mich.

[21] Appl. No.: 975,173

[22] Filed: Nov. 12, 1992

Related U.S. Application Data

[62] Division of Ser. No. 594,243, Oct. 9, 1990, Pat. No. 5,182,340.

[51] Int. Cl.$^5$ .................. C08L 63/02; C08L 63/04
[52] U.S. Cl. .......................... 525/525; 525/481; 525/485; 525/486; 525/488; 525/489; 525/510
[58] Field of Search ............... 528/391; 525/485, 486, 525/488, 511, 481, 489, 510, 513, 523, 525, 533, 535

[56] References Cited

U.S. PATENT DOCUMENTS

| | | | |
|---|---|---|---|
| 3,378,522 | 4/1968 | Martin | 549/90 |
| 4,748,083 | 5/1988 | Widmer et al. | 549/90 |
| 4,962,163 | 10/1990 | Hefner, Jr. et al. | 525/463 |
| 5,024,785 | 6/1991 | Hefner, Jr. et al. | 252/299.01 |
| 5,189,117 | 2/1993 | Hefner, Jr. | |

FOREIGN PATENT DOCUMENTS

| | | |
|---|---|---|
| 0361859 | 4/1990 | European Pat. Off. |
| 0379055 | 7/1990 | European Pat. Off. |
| 0379057 | 7/1990 | European Pat. Off. |

OTHER PUBLICATIONS

Bell and Ku, "Epoxy/Episulfide Resins," *Crosslinked Epoxies,* Walter de Gruyter and Co., New York, NY, 1987, pp. 3-26.
Vecera and Spacek, "Preparation and Reactivity of Thiiranes," *Crosslinked Epoxies,* Walter de Gruyter and Co., New York, NY, 1987, pp. 73-80.
"Ferroelectric Liquid Crystals and Dopants Containing the Chiral Thiirane Unit, A Comparison With Analogous Oxiranes" by G. Scherowsky and J. Gay, *Liquid Crystals,* vol. 5, pp. 1253-1258, (1989).
Copending applications Ser. No. 556,607 filed Jul. 13, 1990 by Jimmy D. Earls Paul M. Puckett and Robert E. Hefner, Jr. titled "Curable Compositions Containing Mesogenic Advanced Resin Compositions and Curing Agent Therefore and Cured Products".
Copending application Ser. No. 553,930 filed Jul. 13, 1990 by Jimmy D. Earls, Paul M. Puckett, and Robert E. Hefner, Jr. titled "Advanced Resin Compositions Containing Mesogenic Moieties".
Copending application Ser. No. 297,894 filed Jan. 17, 1989 by Paul M. Puckett, Jimmy D. Earls and Michael B. Cavitt, titled "Dihydroxybenzophenone Oximes, Their Preparation and Rearrangement to the Anilide".
Copending application Ser. No. 380,936 filed Jul. 17, 1989 by Robert E. Hefner, Jr. and Jimmy D. Earls titled "Mesogenic Cyanate Functional Maleimides and Thermosets Thereof".
Copending application Ser. No. 380,938 filed Jul. 17, 1989 (same date as above identified application) by Robert E. Hefner, Jr., Jimmy D. Earls and Paul M. Puckett, titled "Mesogenic Polycyanates and Thermosets Thereof".
Copending application Ser. No. 562,289 filed Aug. 3, 1990 by Robert E. Hefner, Jr. and Jimmy D. Earls, titled "Adducts of Epoxy Resins and Active Hydrogen Containing Compounds Containing Mesogenic Moieties".
Copending application Ser. No. 562,787 filed Aug. 3, 1990 by Robert E. Hefner, Jr. and Jimmy D. Earls, titled "Polymer Modified Adducts of Epoxy Resins and Active Hydrogen Containing Compounds Containing Mesogenic Moieties".
Copending Application Ser. No. 562,182 filed Aug. 3, 1990 by Jimmy D. Earls, Robert E. Hefner, Jr. and Paul M. Puckett titled "Curable Mixtures of Mesogenic Epoxy Resins and Mesogenicpolyamines and Cured Compositions".

*Primary Examiner*—Robert E. Sellers

[57] ABSTRACT

A rodlike mesogenic moiety-containing polythiirane resin is blended with an epoxy resin and when cured with a curing agent is useable in molding applications.

6 Claims, No Drawings

BLENDS OF MESOGENIC POLYTHIIRANES AND EPOXY RESINS

CROSS-REFERENCE TO RELATED APPLICATION

This application is a division of application Ser. No. 07/594,243 filed Oct. 9, 1990, now U.S. Pat. No. 5,182,340, which is incorporated herein by reference in its entirety.

FIELD OF THE INVENTION

The present invention pertains to polythiiranes containing one or more rodlike mesogenic moieties, curable compositions and cured compositions thereof and process.

BACKGROUND OF THE INVENTION

Thiirane or episulfide resins prepared from the corresponding glycidyl ether based resins have been found to possess higher reactivity (shorter gel time) to aliphatic and cycloaliphatic amine curing agents as well as polyamidoamines. Reactivity to aromatic amine curing agents has been found to be reduced. Additionally, the curing of the thiirane resin proceeds at a lower temperature that that of the corresponding epoxy resin. Incremental enhancement of some mechanical properties of cured thiirane resins or blends of thiirane and epoxy resins occurs over those of the epoxy resin, per se.

The polythiirane resin compositions of the present invention contain one or more rodlike mesogenic moieties. The polythiirane resins exhibit ordering of the molecular chains in one or more of the melt phase, advanced compositions thereof, cured compositions thereof or the homopolymers (self-cured) thereof. This morphology is susceptible to flow induced orientation during processing which can result in enhanced unidirectional mechanical properties. The rodlike mesogenic structures incorporated into the polythiirane provide the improvement in one or more of the properties. The property improvements obtained with polythiirane resins of this type can be unidirectionally enhanced by electric or magnetic fields or by drawing and/or shear forces applied during processing and/or curing.

SUMMARY OF THE INVENTION

One aspect of the present invention concerns thiirane resins containing an average of more than one thiirane group and at least one rodlike mesogenic moiety per molecule.

Another aspect of the present invention concerns advanced thiirane resins containing at least one rodlike mesogenic moiety per molecule which are prepared by reacting (A) at least one thiirane resin containing an average of more than one thiirane group and at least one rodlike mesogenic moiety per molecule: with (B) at least one compound having an average of more than one active hydrogen atom per molecule:

wherein components (A) and (B) are present in quantities which provide a ratio of groups reactive with a thiirane group per thiirane group of from about 0.001:1 to about 1.05:1.

Another aspect of the present invention concerns a blend comprising (A) at least one thiirane resin containing an average of more than one thiirane group and at least one rodlike mesogenic moiety per molecule: and (B) at least one of (1) one or more compounds containing only one thiirane group per molecule, (2) one or more compounds containing only one vicinal epoxide group per molecule, or (3) a combination of (1) and (2).

Another aspect of the present invention concerns a blend comprising (A) at least one thiirane resin containing an average of more than one thiirane group and at least one rodlike mesogenic moiety per molecule: and (B) an epoxy resin containing an average of more than one vicinal epoxide group per molecule.

A further aspect of the present invention concerns a curable composition comprising (I) any of the aforementioned thiirane resins or blends containing same and (II) a curing amount of a suitable curing agent therefor.

A further aspect of the present invention concerns the product or article resulting from curing the aforementioned curable compositions.

A further aspect of the present invention concerns the product or article resulting from curing by heating a composition comprising as the only reactive component therein at least one of (A) at least one thiirane resin containing an average of more than one thiirane group and at least one rodlike mesogenic moiety per molecule or:

(B) at least one advanced thiirane resin containing at least one rodlike mesogenic moiety per molecule which is prepared by reacting (1) at least one thiirane resin containing an average of more than one thiirane group and at least one rodlike mesogenic moiety per molecule: with (2) at least one compound having an average of more than one active hydrogen atom per molecule;

wherein components (1) and (2) are present in quantities which provide a ratio of groups reactive with a thiirane group per thiirane group of from about 0.001:1 to about 1.05:1:

(C) a combination of (A) and (B): or (D) a combination of either (A) or (B) or both (A) and (B) with a monothiirane compound.

A still further aspect of the present invention concerns a process for the preparation of thiirane resins (polythiiranes) containing at least one rodlike mesogenic moiety per molecule comprises reacting (1) an epoxy resin (polyepoxide) containing an average of more than one vicinal epoxy group per molecule: with (2) a sulfur-containing compound selected from the group consisting of inorganic thiocyanates, thioureas, N-alkylbenzothiazol-2-thiones and phosphine sulfides.

DETAILED DESCRIPTION OF THE INVENTION

Thiirane Resins

Suitable thiirane resins containing an average of more than one thiirane group and at least one rodlike mesogenic moiety per molecule include those represented by the Formulas I, II or III:

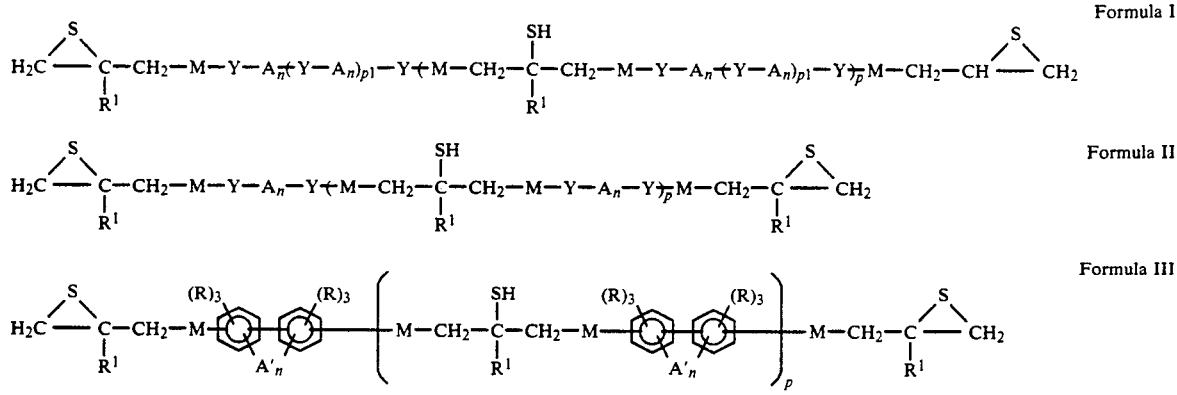

Formula I
Formula II
Formula III wherein each Y is independently

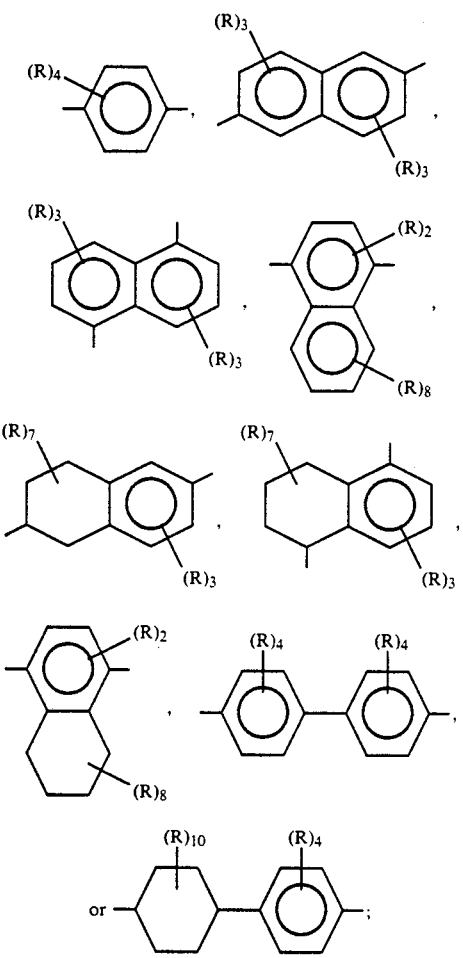

each M is independently (a) —O—, —S—, or —CO—O— where the single bonded oxygen atom attached to the carbon atom of —CO—O— is attached to the $-CH_2-\underset{R^1}{C}\diagdown\underset{}{\overset{S}{\diagup}}CH_2$ group, or (b)

—CO—O—(CHR$^a$—CHR$^a$—O)$_m$,

-continued

—O—(CHR$^a$—CHR$^a$—O)$_m$, or

—S—(CHR$^a$—CHR$^a$—O)$_m$ where a single bonded oxygen atom is attached to the $-CH_2-\underset{R^1}{C}\diagdown\underset{}{\overset{S}{\diagup}}CH_2$ group;

each R$^a$ is independently hydrogen or an alkyl or haloalkyl group containing from 1 to about 2 carbon atoms with the proviso that only one R$^a$ group can be a haloalkyl group; m has a value from 1 to about 100, preferably from 1 to about 20, more preferably from 1 to about 10, most preferably from 1 to about 5; each A is independently a direct single bond, —CR$^1$=CR$^1$—, —C≡C—, —N=N—, —CR$^1$=N—, —O—CO—, —NR$^1$—CO—, —CR$^1$=N—N=CR$^1$—, —CR$^1$=CR$^1$—CO—, —N=CR$^1$—, —CO—O—, —CO—NR$^1$—, —CO—CR$^1$=CR$^1$—, —CO—O—N=CR$^1$—, —CR$^1$=N—O—OC—, —CO—NR$^1$—NR$^1$—OC—, —CR$^1$=CR$^1$—O—OC—, —CO—O—CR$^1$=CR$^1$—, —O—OC—CR$^1$=CR$^1$—, —CR$^1$=CR$^1$—CO—O—, —CHR$^1$—O—CO—CR=$^{CR1}$—, —CR$^1$=CR$^1$CO—O—CHR$^1$—, —CHR$^1$—CO—O—CR$^1$=CR$^1$—, —CR$^1$=CR$^1$—O—CO—CHR$^1$—, —CO—S—, —S—OC—, —CH$_2$—CH$_2$—CO—O—, —O—OC—CH$_2$—CH$_2$—, —C≡C—C≡C—, —CR$^1$=CR$^1$—CR$^1$=CR$^1$—,

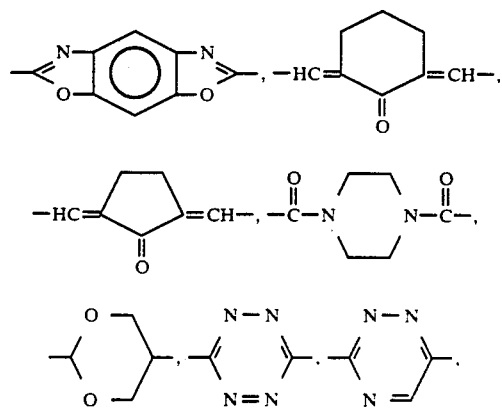

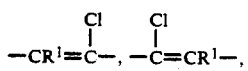

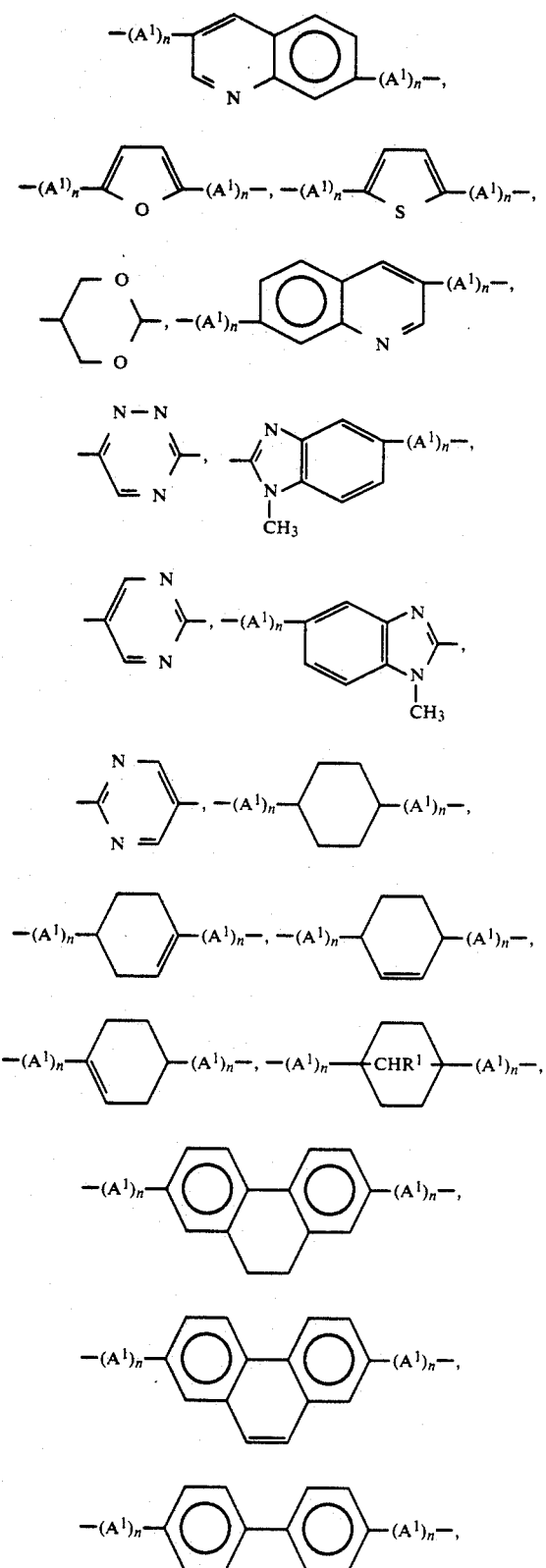

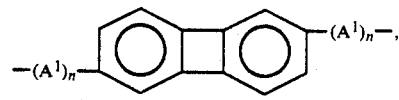

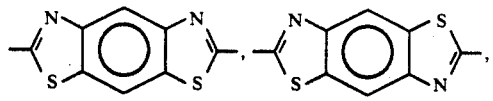

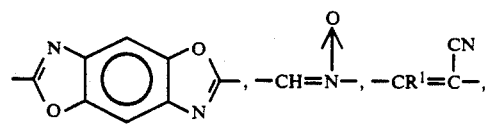

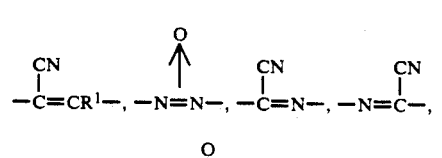

A' is independently a divalent hydrocarbyl group having from 1 to about 10, preferably from 1 to about 4, carbon atoms: each $A^1$ is independently a

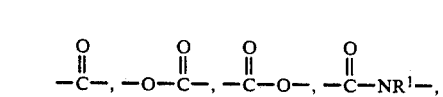

each R is independently hydrogen or a hydrocarbyl or hydrocarbyloxy group having from 1 to about 10, preferably 1 to about 4, carbon atoms, a halogen atom, preferably chlorine or bromine, a nitro group, a nitrile group, a phenyl group or a —CO—$R^1$ group: each $R^1$ is independently hydrogen or a hydrocarbyl group having 1 to about 3 carbon atoms: n has a value of zero or one: p has a value from zero to about 30, preferably from zero to about 5: and $p^1$ has a value from 1 to about 30, preferably from 1 to about 3. The aromatic rings can also contain one or more heteroatoms selected from N, O, S and the like.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic or cycloaliphatic groups can be saturated or unsaturated. When applied to the A' group of Formula III, the hydrocarbyl group can also contain one or more heteroatoms selected from N, O, S and the like. Likewise, the term hydrocarbyloxy means a hydrocarbyl group having an oxygen linkage between it and the carbon atom to which it is attached.

The thiirane resins containing a rodlike mesogenic moiety include, for example, those represented by the aforementioned Formulas I, II or III wherein at least 80 percent of the molecules are para substituted by both the bridging groups (—A—) and the substituent containing the thiirane groups

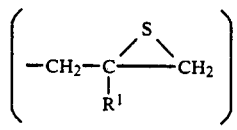

as well as the substituent containing a secondary thiol alkylidene group(s)

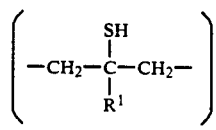

which are present when p has a value greater than zero.

For Formula III, it is to be understood that para substitution is with respect to the direct bond between the aromatic rings. The bridging groups (—A—) form a rigid central linkage between the aromatic ring pairs. To optimize the aspect ratio of said rodlike mesogenic functionalities, it is preferred that the aromatic ring substituents (R in Formulas I, II and III) are hydrogen or methyl groups.

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

Representative thiirane resins containing a rodlike mesogenic moiety include, for example, the dithiirane ethers of 4,4'-dihydroxybiphenyl, 4,4'-dihydroxystilbene, 4,4'-dihydroxydiphenylacetylene, 4,4'-dihydroxydiphenylazomethine, 4,4'-dihydroxyazobenzene, 4,4'-dihydroxyazoxybenzene, 4,4'-bis((4-hydroxy)phenoxy)-diphenyl, 3,3',5,5'-tetramethyl-4,4'-dihydroxydiphenyl, 3,3',5,5'- tetrachloro-4,4'-dihydroxydiphenyl, 2,2',6,6'-tetramethyl-4,4'-dihydroxydiphenyl, bis (4-hydroxyphenyl)terephthalate, N,N'-bis(4-hydroxyphenyl)-terephthalamide, 4-hydroxyphenyl-4-hydroxybenzoate, 4,4'-dihydroxybenzanilide, N-methyl-4,4'-dihydroxybenzanilide, 4,4'-dihydroxy-alpha-methylstilbene, 4,4'-dihydroxychalcone, 4,4'-dihydroxy-alpha-cyanostilbene, 2,2'-dimethyl-4,4'-dihydroxyazoxybenzene, 4,4'-dihydroxy-a,a'-dimethylstilbene, 4,4''-dihydroxybiphenylbenzoate, 4,4'-dihydroxy-a,a'-diethylstilbene, bis(4'-hydroxyphenyl)-1,4-benzenediimine, bis(4'-hydroxybiphenyl)terephthalate, the dithiirane ethers of the dihydric phenols represented by the following formulas:

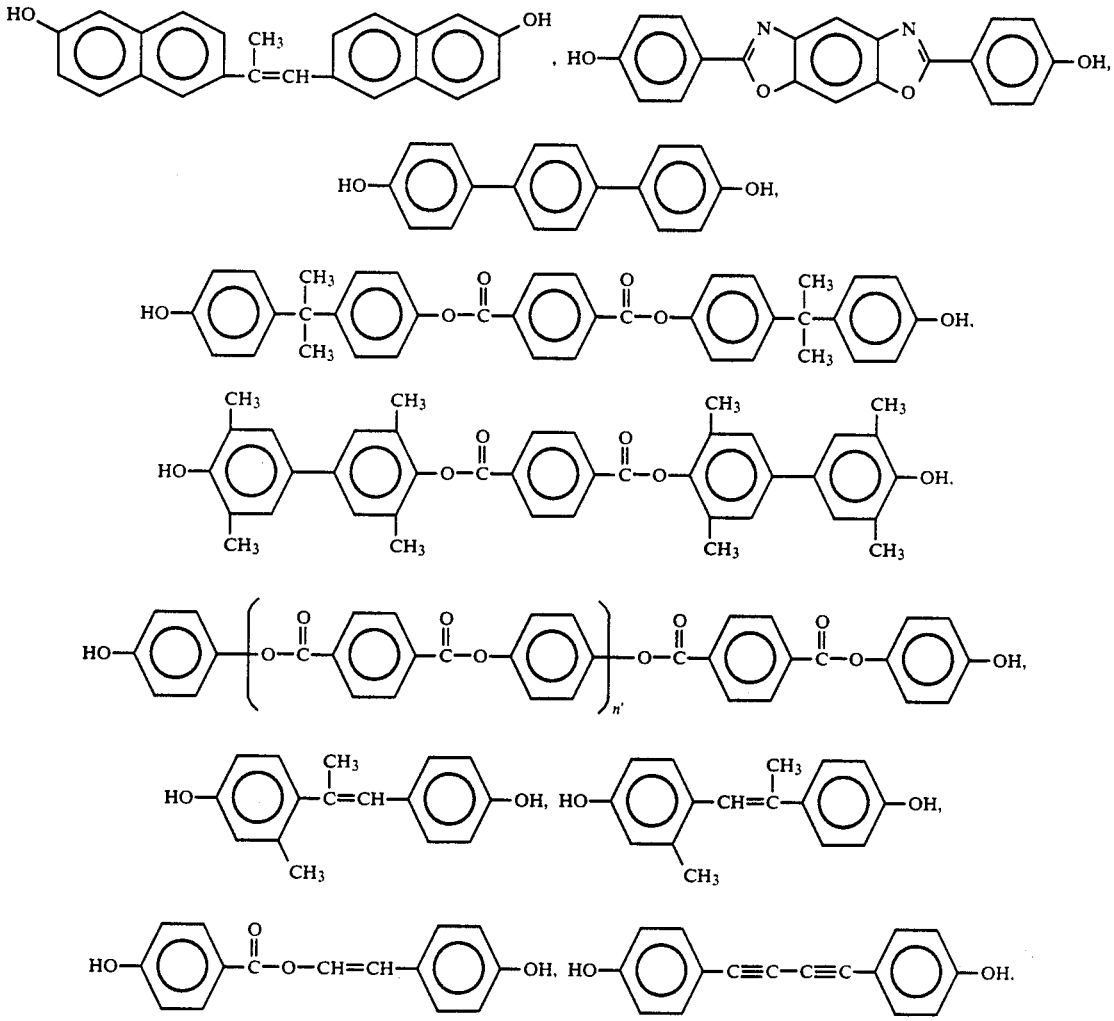

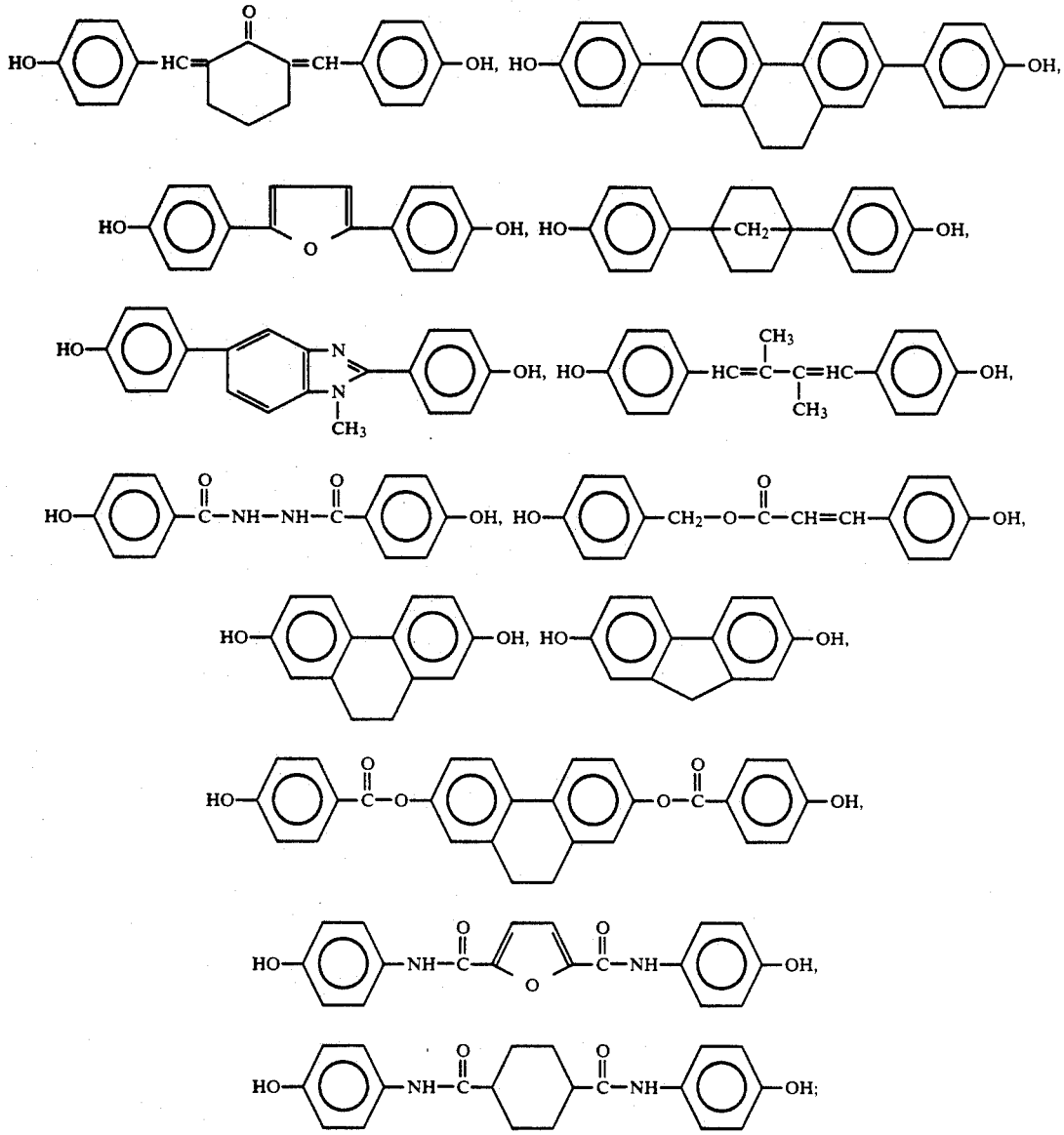

wherein n' has a value from 1 to about 10. Also suitable are the products resulting from advancing the aforementioned dithiiranes with aromatic dihydroxyl or carboxylic acid containing compounds including, for example, all of the previously listed diphenol precursors to the dithiiranes containing a rodlike mesogenic moiety: mixtures thereof and the like.

Additional representative thiirane resins containing a rodlike mesogenic moiety include, for example, the tetrathiirane glycidyl amines of 4,4'-diaminostilbene, 4,4'-diamino-alpha-methylstilbene, 4,4'-diaminobenzanilide, 4-aminophenyl-4-aminobenzoate: the dithiirane glycidyl amines of N,N'-diethyl-4,4'-diaminostilbene, N,N'-dimethyl-4,4'-diaminobenzanilide: the dithiirane glycidyl thioethers of 4,4'-stilbenedithiol, 4,4'-alpha-methylstilbenedithiol, 4,4'-benzanilidedithiol: the dithiirane glycidyl esters of 4,4'-stilbenedicarboxylic acid, 4,4'-alpha-methylstilbenedicarboxylic acid, 4,4'-benzanilidedicarboxylic acid: the dithiirane glycidyl ethers of the bis(2-hydroxyethylether)s of 4,4'-dihydroxystilbene, 4,4'-dihydroxy-alpha-methylstilbene: the dithiirane glycidyl thioether ethers of the bis(2-hydroxyethylthioether)s of 4,4'-stilbenedithiol, 4,4'-alpha-methylstilbenedithiol: the dithiirane glycidyl ester ethers of the bis(2-hydroxyethylester)s of 4,4'-stilbenedicarboxylic acid, 4,4'-alpha-methylstilbenedicarboxylic acid: mixtures thereof and the like. Also suitable are the products resulting from advancing the aforementioned di/polythiiranes with aromatic dihydroxyl or dicarboxylic acid containing compounds.

Preparation Of Thiirane Resins

Epoxidation of di- and polyhydroxy aromatic compounds (or di- and polycarboxylic acids) used to prepare the thiirane resins of the present invention can be performed by the known methods described in Handbook of Epoxy Resins by Lee and Neville, McGraw-Hill, 1967: Jpn. Kokai Tokkyo Koho JP 62 86,484 (87 96,484): EP 88-008358/92 and Journal of Applied Polymer Science, Vol. 23, 1355–1372 (1972) all of which are incorporated herein by reference. This usually includes reacting the respective di- or polyhydroxy aromatic compound (or di- and polycarboxylic acids) with an excess of an epihalohydrin such as, for example, epichlorohydrin or methyl epichlorohydrin, at a temperature of from about 0° C. to about 100° C., preferably from about 20° C. to about 65° C. followed by dehydrohalogenation with a basic-acting material such as, for example, an alkali metal hydroxide, typically sodium hydroxide, at a temperature of from about 0° C. to about 100° C., preferably from about 20° C. to about 65° C. and finally recovering the resulting glycidyl ether product. For the production of polyepoxides from di- and polyhydroxy aromatic compounds possessing functional groups or linkages that are sensitive to hydrolysis under the reaction conditions employed in certain epoxidation chemistries, alternate techniques of preparation may be employed. As a typical example, Dhein, et al. in U.S. Pat. No. 4,762,901 teaches preparation of the diglycidyl ether of the bisphenol represented by the following formula

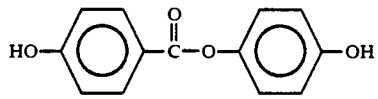

which is a compound containing an ester linkage known to be sensitive to hydrolysis, using an anhydrous epoxidation technique. This technique employs azeotropic removal of water/epichlorohydrin concurrent with the controlled addition of aqueous sodium hydroxide to a reaction mixture consisting of epichlorohydrin, a diphenol, a phase transfer catalyst such as, for example, benzyltrimethylammonium chloride, and optionally, solvent(s) may also be employed. It is advantageous to conduct such anhydrous epoxidation reactions under a vacuum to facilitate the azeotropic removal of water. The azeotropic removal of water is usually conducted at temperatures of from about 20° C. to about 100° C., preferably from about 30° C. to about 65° C. It is also operable and advantageous to utilize sodium hydroxide free of water a the alkali metal hydroxide reactant. In order to control reaction exotherm, the solid sodium hydroxide is typically added in aliquots as a powder to the epoxidation reaction mixture. A typical anhydrous epoxidation technique is described by Wang, et al. in U.S. Pat. No. 4,499,255 which is incorporated herein by reference in its entirety.

Another specific anhydrous epoxidation technique involves catalytic coupling of the di- or polyhydroxyl containing compound with an epihalohydrin, typically using as a catalyst one or more of the aforementioned ammonium halides. The resultant solution of halohydrin in excess epihalohydrin is then treated with finely pulverized potassium carbonate to effect dehydrohalogenation to the epoxy resin.

The polyepoxide compounds (epoxy resins) containing a rodlike mesogenic moiety are converted to the thiirane resins (polythiirane compounds) containing a rodlike mesogenic moiety of the present invention via reaction of the epoxide groups therein with suitable sulfur containing compounds such as, for example, inorganic thiocyanates, thioureas, N-alkylbenzothiazol-2-thiones such as N-methylbenzothiazol-2-thione/trifluoroacetic acid or a phosphine sulfide such as triphenylphosphine sulfide/trifluoroacetic acid.

Reaction conditions for conversion of the epoxide group to the thiirane group are given by Bell and Ku in the article "Epoxy/Episulfide Resins" pages 3 to 26 and by Vecera and Spacek in the article "Preparation and Reactivity of Thiiranes", pages 73 to 80 both published in *Crosslinked Epoxies*, Sedlacek and Kahwec (editors), by Walter de Gruyter, New York (1987): Chan and Finkenbine, *Journal of the American Chemical Society*, 94, 2880 (1972) and Calo, Lopez, Marchese and Pesce, *Journal of the Chemical Society, Chemical Communications*, 621 (1975), all of which are incorporated herein by reference.

The reaction is usually conducted at temperatures of from about 5° C. to about 100° C., preferably from about 20° C. to about 60° C., for a time sufficient to complete the reaction, usually from about one hour to about forty eight hours, preferably from about four to about twenty four hours. The higher reaction temperatures typically require shorter times whereas the lower reaction temperatures typically require longer times to complete the reaction.

Advanced Thiirane Resins

Advancement reaction of the thiirane resins containing a rodlike mesogenic moiety with one or more compounds having an average of more than one active hydrogen atom per molecule can be performed by the known methods described in the aforementioned *Handbook of Epoxy Resins*. This usually includes combining the compound(s) having an average of more than one group reactive with a thiirane group per molecule and the thiirane resin(s) with the application of heat and mixing to effect the advancement reaction. A catalyst is frequently added to facilitate the advancement reaction.

The thiirane resin(s) and the compound(s) having an average of more than one group reactive with a thiirane group per molecule are reacted in amounts which provide suitably from about 0.001:1 to about 1.05:1, more suitably from about 0.05:1 to about 0.9:1, most suitably from about 0.10:1 to about 0.50:1 active hydrogen atoms per thiirane group.

By the term "compounds having an average of more than one active hydrogen atom per molecule" it is meant that the compound contains hydrogen atoms which are reactive with a thiirane group.

Suitable compounds having an average of more than one active hydrogen atom per molecule which can be employed to prepare the advanced resin compositions of the present invention may contain one or more rodlike mesogenic moieties or may be free of said moieties. Suitable compounds having an average of more than one active hydrogen atom per molecule which can be employed to prepare the advanced resin compositions of the present invention include, for example, diphenols, thiodiphenols, dicarboxylic acids and compounds containing one primary amine or amide group or two secondary amine groups such as those represented by the Formulas IV, V, VI or VII:

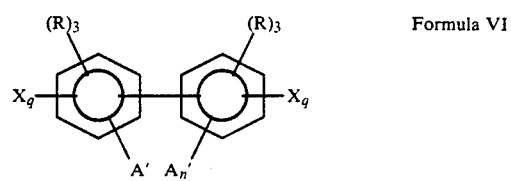

Formula IV

Formula V

Formula VI

-continued

H₂N—R³   Formula VII wherein X is independently a —OH, —COOH, —SH or —NHR¹ group; q has a value of 1 with the proviso that when one q=1 and one q=0, one X may be —NH₂, —H₂N—SO₂—, —H₂N—CO— or H₂N—R³—O— and the other X becomes R; R³ is an aliphatic, cycloaliphatic, polycycloaliphatic or alkylsubstituted cycloalphaic orpolycycoaliphatic group having from 1 to about 12, preferably 1 to about 4, carbon atoms, q has a value of zero or one, each Y is independently

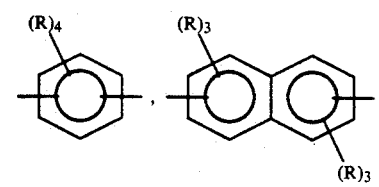

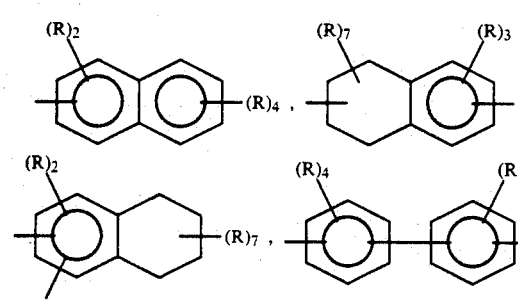

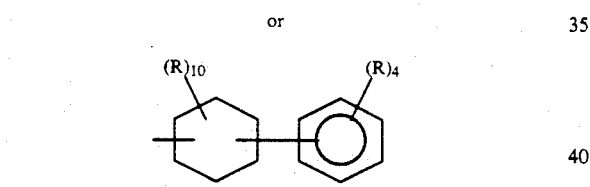

or

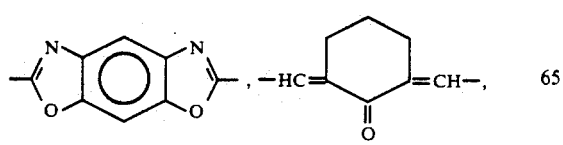

each A is independently a direct single bond, a divalent hydrocarbyl group having from 1 to about 20, preferably from 1 to about 14, carbon atoms, —O—, —CO—, —SO—, —SO₂—, —S—, —S—S—, —CR¹=CR¹—, —C≡C—, —N=N—, —CR¹=N—, —O—CO—, —NR¹—CO—, —CR¹=N—N=CR¹—, —CR¹=C-R¹—CO—, —N=CR¹, —CO—O—, —CO—NR¹—, —CO—CR¹=CR¹—, —CO—O—N=CR¹—, —CR¹=N—O—OC—, —CO—NR¹—NR¹—OC—, —CR¹=CR¹—O—OC—, —CO—O—CR¹=CR¹—, —O—OC—CR¹=CR¹—, —CR¹=CR¹—CO—O—, —CHR¹—O—CO—CR¹=CR¹—, —CR¹=C-R¹—CO—O—CHR¹—, —CHR¹—CO—O—CR¹=C-R¹—, —CR¹=CR¹—O—CO—CHR¹—, —CO—S—, —S—OC—, —CH₂—CH₂—CO—O—, —O—O-C—CH₂—CH₂—, —C≡C—C≡C—, —CR¹=C-R¹—CR¹=CR¹—,

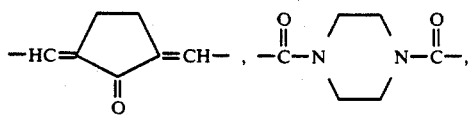

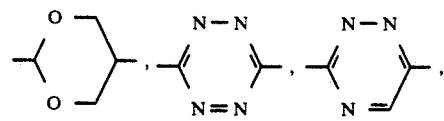

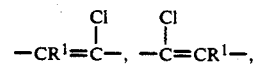

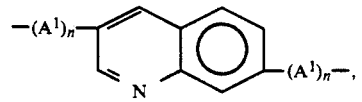

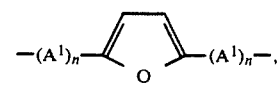

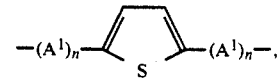

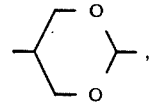

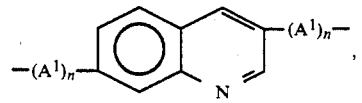

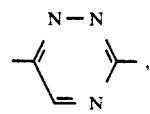

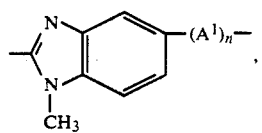

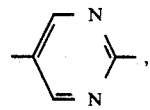

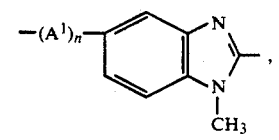

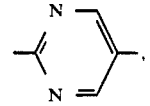

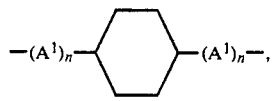

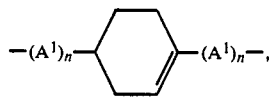

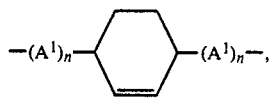

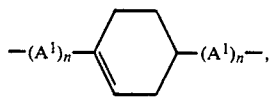

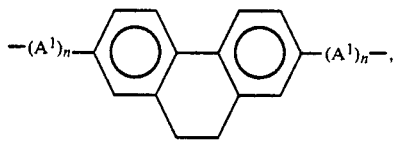

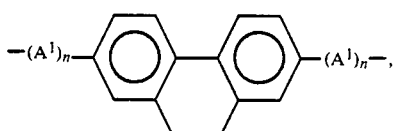

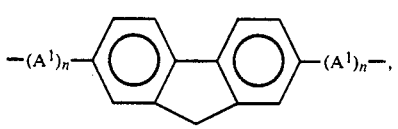

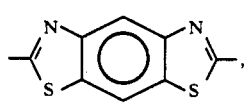

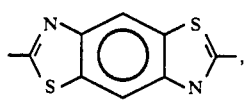

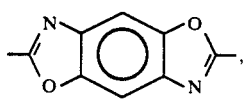

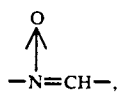

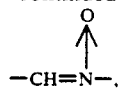

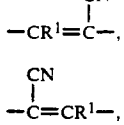

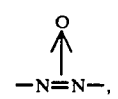

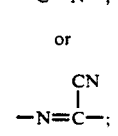

or

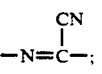

and A', $A^1$, $R^1$ and n are as hereinbefore defined. The aromatic rings can also contain one or more heteroatoms selected from N, O or S and the like.

Particularly suitable hydroxyl containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1-carboxy)benzene, 4,4'-bis(4''-hydroxyphenyl-1''-carboxy)biphenyl, mixtures thereof and the like.

Particularly suitable thiol containing compounds include, for example, 4,4'-dithiodiphenylmethane, 4,4'-isopropylidenedithiophenol, 4,4'-dithio-α-methylstilbene, mixtures thereof and the like.

Particularly suitable carboxylic acid containing compounds include, for example, terephthalic acid, 4,4'-benzanilide dicarboxylic acid, 4,4'-phenylbenzoate dicarboxylic acid, 4,4'-stilbenedicarboxylic acid and mixtures thereof and the like.

Particularly suitable primary amine or amide containing compounds include, for example, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-amino-phenyl-1-carboxamide, phenyl-4-aminobenzoate, biphenyl-4-aminobenzoate, 1-phenyl-4'-aminophenyl-terephthalate, mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate.acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate.acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990: 3,547,881: 3,637,590: 3,843,605: 3,948,855: 3,956,237: 4,048,141: 4,093,650: 4,131,633: 4,132,706: 4,171,420: 4,177,216 and 4,366,295, all of which are incorporated herein by reference.

The amount of advancement catalyst depends upon the particular reactants and catalyst employed: however, it is usually employed in quantities of from about 0.03 to about 3, preferably from about 0.03 to about 1.5, most preferably from about 0.05 to about 1.5 percent by weight based upon the weight of the thiirane containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture.

The advancement of the polythiiranes containing one or more rodlike mesogenic moieties with compounds having an average of more than one active hydrogen atom per molecule is employed to chain extend and/or branch the resin. This chain extension and/or branching is required for some rodlike mesogen containing resin compositions in order to obtain liquid crystal character. The advancement of the rodlike mesogenic polythiiranes can also be used to modify the temperature range in which a particular resin is liquid crystalline and to control the degree of crosslinking during the final curing.

Curing Agents

The compositions of the present invention containing an average of more than one vicinal thiirane group and at least one rodlike mesogenic moiety per molecule can be cured with any suitable curing agent for curing thiirane or epoxy resins such as, for example, primary and secondary polyamines, carboxylic acids and anhydrides thereof, aromatic hydroxyl containing compounds, imidazoles, guanidines, urea-aldehyde resins, melamine-aldehyde resins, alkoxylated urea-aldehyde resins, alkoxylated melamine-aldehyde resins, aliphatic amines, cycloaliphatic amines, aromatic amines, combinations thereof and the like. Particularly suitable curing agents include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylmethane, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

The curing agents are employed in amounts which will effectively cure the composition: however, these amounts will depend upon the particular polythiirane and curing agent employed. Generally, suitable amounts include, for example, from about 0.50:1 to about 1.2:1 equivalents of curing agent per equivalent of thiirane resin.

The polythiiranes containing one or more rodlike mesogenic moieties can also be "self-cured", that is subjected to heat, until reaction of thiirane moieties occurs. It is felt that the self-curing results from initial opening of the thiirane ring to form a stable sulfide ion which subsequently anionically attacks another thiirane ring. It is beneficial to partially (B-stage) or totally homopolymerize (self-cure) the polythiiranes containing one or more rodlike mesogenic moieties to produce resin compositions possessing liquid crystal character.

Monothiirane And Monoepoxide Compounds

Monothiirane and/or monoepoxide compounds can be employed as reactive diluents for the polythiiranes of the present invention. The monothiirane and/or monoepoxide compounds may contain one or more rodlike mesogenic moieties or may be free of said rodlike mesogenic moieties. Preparation of monothiirane compounds containing a rodlike mesogenic unit which can be employed as reactive diluents herein is taught by Scherowsky and Gay, *Liquid Crystals*, 5, 4, 1253 (1989) which is incorporated herein by reference.

The monothiirane and/or monoepoxide compound(s) are employed in amounts which provides the composition with the viscosity and reactivity profile desired for the particular purpose in which the composition is being employed. Usually the amount of monothiirane and/or monoepoxide compound(s) is from about 1 to about 99, preferably from about 5 to about 40, percent by weight based upon the combined weight of all compounds containing thiirane and/or epoxide groups.

Epoxy Resins (Polyepoxides)

The rodlike mesogenic thiirane resins (polythiiranes) of the present invention can also be employed for the purpose of improving the properties of polyepoxide resins. Generally, suitable amounts of rodlike mesogenic polythiiranes are from about 1 to about 99, more suitably from about 10 to about 80, most suitably from about 10 to about 50 weight percent based on the total weight of the combined resins.

Suitable epoxy resins (polyepoxides) which can be blended with the thiirane resins (polythiiranes) include any compound containing an average of more than one vicinal epoxide group per molecule. Suitable such epoxy resins (polyepoxides) include, for example, aromatic epoxides, aliphatic epoxides, and cycloaliphatic epoxides and the like. Particularly suitable epoxy resins (polyepoxides) include the diglycidyl ethers of: (a) compounds containing one or more aromatic rings and two or more aromatic hydroxyl groups per molecule: (b) compounds which are the result of reacting an alkylene oxide or monoglycidyl ether compound with the compounds of (a): (c) aliphatic diols which contain ether oxygen atoms or which are free of ether oxygen atoms: and (d) cycloaliphatic compounds containing more than one hydroxyl group per molecule.

Particularly suitable epoxy resins (polyepoxides) include, for example, (a) the diglycidyl ethers of resorcinol, bisphenol A, 4,4'-dihydroxydiphenylmethane, 4,4'-dihydroxybenzophenone, 3,3',5,5'-tetrabromobisphenol A, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachlorobisphenol A, 3,3'-dimethoxybisphenol A, 4,4'-dihydroxy-alpha-methylstilbene, 4,4'-dihydroxybenzanilide, 4,4'-dihydroxyazoxybenzene, 4,4'-dihydroxybiphenyl: (b) the triglycidyl ether of tris(hydroxyphenyl)methane: (c) the polyglycidyl ethers of a phenol or alkyl or halogen substituted phenolaldehyde acid catalyzed condensation product (novolac resins): the polyglycidyl ether of the condensation product of a dicyclopentadiene or an oligomer thereof and a phenol or alkyl or halogen substituted phenol: (d) the advancement reaction product of the aforesaid di- and polyglycidyl ethers with aromatic di- or polyhydroxyl- or carboxylic acid- containing compounds including, for example, bisphenol A (4,4'-isopropylidenediphenol), o-, m-, p-dihydroxybenzene, 2,4-dimethylresorcinol, 4,4'-dihydroxybiphenyl, 4,4'-dihydroxy-alpha-methylstilbene, 4,4'-dihydroxybenzanilide, 4-chlororesorcinol, tetramethylhydroquinone, 1,1-bis(4-hydroxyphenyl)ethane, 1,1-bis(4-hydroxyphenyl)-1-phenylethane, 4,4'-dihydroxydiphenyl ether, 3,3',5,5'-tetramethyldihydroxydiphenyl ether, 3,3',5,5'-tetrachlorodihydroxydiphenyl ether, 4,4'-bis(p-hydroxyphenyl isopropyl)diphenyl ether, 4,4'-bis(p-hydroxyphenoxy)benzene, 4,4'-bis(p-hydroxyphenoxy)diphenyl ether, 4,4'-bis(4(4-hydroxyphenoxy)phenyl sulfone)-diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)methane, dicyclopentadiene diphenol, tricyclopentadiene diphenol: and (e) any combination of any of the aforementioned epoxy resins and the like.

Orientation

During processing and/or cure of the polythiirane resin compositions into a part, electric or magnetic fields or drawing and/or shear forces can be applied for the purpose of orienting the rodlike mesogenic and/or liquid crystal moieties contained or developed therein which in effect improves the mechanical properties. As specific examples of these methods, Finkelmann, et al, *Macromol. Chem.*, 180, 803-806 (March 1979) induced orientation in thermotropic methacrylate copolymers containing rodlike mesogenic side chain groups decoupled from the main chain via flexible spacers in an electric field. Orientation of rodlike mesogenic side chain groups decoupled from the polymer main chain via flexible spacers in a magnetic field has been demonstrated by Roth and Kruecke, *Macromol. Chem.*, 187, 2655-2662 (November 1986). Magnetic field induced orientation of rodlike mesogenic main chain containing polymers has been demonstrated by Moore, et al, *ACS Polymeric Material Sciences and Engineering*, 52, 84-86 (April-May 1985). Magnetic and electric field orientation of low molecular weight rodlike mesogenic compounds is discussed by W. R. Krigbaum in *Polymer Liquid Crystals*, pages 275-309 (1982) published by Academic Press, Inc. All of the above are incorporated herein by reference in their entirety.

In addition to orientation by electric or magnetic fields, polymeric mesophases can be oriented by drawing and/or shear forces which are induced by flow through dies, orefices, and mold gates. A general discussion for orientation of thermotropic liquid crystal polymers by this method is given by S. K. Garg and S. Kenig in *High Modulus Polymers*, pages 71-103 (1988) published by Marcel Dekker, Inc. For the mesomorphic systems based on the epoxy resin compositions, this shear orientation can be produced by processing methods such as injection molding, extrusion, pultrusion, filament winding, filming and prepreging.

Other Components

The rodlike mesogenic polythiiranes of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color: however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, combinations thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include, glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitably from about zero to about 95, more suitably from about 10 to about 80, most suitably from about 40 to about 60 percent by weight based upon the weight of the total composition.

The thiirane resins (polythiiranes) of the present invention can be employed in coating, casting, encapsulation, electonic or structural laminate or composite, filament winding, molding, and the like applications.

The following examples are illustrative of the present invention, but are not to be construed as to limiting its scope in an manner.

EXAMPLE 1

A. Synthesis of
3,3',5,5'-Tetramethyl-4,4'-Dihydroxy-alpha-methylstilbene 2,6-Dimethylphenol (488.68 grams, 4.0 moles), chloroacetone (192.77 grams, 2.0 moles as chloroacetone) and methylene chloride (300 grams) are added to a two liter glass resin kettle reactor equipped with a chilled water condenser, mechanical stirrer, nitrogen purge (1 liter per minute), thermometer and dry ice-methylene chloride cooling bath and cooled to −10° C. with stirring. The chloroacetone used is a commercial grade containing 96% chloroacetone. Concentrated sulfuric acid (196.16 grams, 2.0 mole) is added dropwise to the stirred solution over a forty six minute period and so as to maintain the reaction temperature between −10° and −11° C. After two hours of post reaction between a −10° to −11° C. temperature range, the light pink colored crystalline slurry is diluted with methylene chloride (1000 milliliters) to provide a solution which is then washed with 1000 milliliters of iced deionized water. The organic solution is separated then washed with a second 1000 milliliter portion of iced deionized water. After separation, the recovered organic solution is rotary evaporated under vacuum using a oil bath heated to 70° C. until the removal of methylene chloride induced the formation of a thick crystalline slurry. The crystalline slurry is added to a 2 liter beaker along with ethanol (350 milliliters) and stirred to provide a solution. Deionized water (250 milliliters) is added to the stirred solution and heating commences. As the temperature of the mixture increases, the stirred mixture begins to clear. Each time clearing is observed, sufficient deionized water is added to induce cloudiness, followed by continuation of the mixing and heating. Once the temperature reaches 80° C., a massive precipitation of white crystalline product occurs and is followed by immediate coalesence of the precipitated product to an oil. The oil layer is recovered by decantation of the water layer and deionized water is again added to the stirred solution as heating commences, in an amount sufficient to induce cloudiness each time clearing is observed. Once the temperature reaches 80° C., a massive precipitation of white crystalline product again occurs. At this time, stirring is stopped and the crystalline slurry is chilled to 4° C. and held therein for 12 hours. The crystalline product is recovered by filtration, combined with deionized water (800 milliliters) then stirred with heating to 90° C. The crystalline product is recovered by filtration, ground to a fine powder, combined with deionized water (800 milliliters) then stirred with heating to 90° C. After recovery by filtration the powder product is dried in a vacuum oven at 100° C. and 5 mm Hg to a constant weight of 363.40 grams. A second crop of crystalline product precipitated from the filtrate from the initial filtration step held at 4° C. is recovered by filtration and provides an additional 25.75 grams of product after washing and drying. Proton magnetic resonance spectroscopy and infrared spectrophotometric analysis confirms the product structure.

B. Epoxidation of
3,3',5,5'-Tetramethyl-4,4'-dihydroxy-alpha-methylstilbene 3,3',5,5'-Tetramethyl-4,4'-dihydroxy-alphamethylstilbene (211.78 grams, 1.50 hydroxyl equivalent) from A. above, epichlorohydrin (693.98 grams, 7.50 moles), deionized water (60.35 grams, 8.0 percent by weight of the epichlorohydrin used) and isopropanol (373.68 grams, 35 percent by weight of the epichlorohydrin used) are added to a two liter glass resin kettle reactor equipped with a chilled water condenser, mechanical stirrer, nitrogen purge (1 liter per minute), thermometer and thermostatically controlled infrared heating lamps and heated to 55° C. with stirring under a nitrogen atmosphere. Once the 55° C. reaction temperature is achieved, sodium hydroxide (54.0 grams, 1.35 mole) dissolved in deionized water (216 grams) is added dropwise to the reactor over a 45 minute period, so as to maintain reaction temperature between 55° and 58° C. Ten minutes after completion of the aqueous sodium hydroxide addition, the stirring is stopped and the aqueous layer which separates from the reaction mixture is pipetted off and discarded. Stirring is resumed and after a total of twenty minutes following completion of the initial aqueous sodium hydroxide addition, a second solution of sodium hydroxide (24.0 grams, 0.60 mole) dissolved in deionized water (96 grams) is added to the reactor over a twenty minute period and so as to maintain the 55° C. reaction temperature. Fifteen minutes after completion of the aqueous sodium hydroxide addition, the recovered reaction mixture is added to a separatory funnel and washed with 500 milliliters of deionized water. The separated organic layer is washed a second time (500 milliliters deionized water), recovered and then rotary evaporated under vacuum for 45 minutes at 110° C. then 30 minutes at 140° C. and 5 mm Hg. The product is recovered (293.84 grams) as a light amber colored, transparent liquid (at 24° C.) with an epoxide equivalent weight of 227.80.

C. Conversion of the Diglycidyl Ether of 3,3',5,5'-Tetramethyl-4,4'-dihydroxy-alpha-methylstilbene to the Dithiirane A portion of the diglycidyl ether of 3,3',5,5'-tetramethyl-4,4'-dihydroxy-alpha-methylstilbene (113.90 grams, 0.50 epoxide equivalent) from B. above, 1,4-dioxane (125 grams) and methanol (125 grams) are added to a one liter glass resin kettle reactor equipped with a chilled water condenser, nitrogen purge (1 liter per minute), thermometer and thermostatically controlled infrared heating lamps and maintained at 21° C. with stirring under a nitrogen atmosphere. A solution of thiourea (0.48 mole, 36.54 grams) in 1,4-dioxane (125 grams) and methanol (125 grams) is added to the reactor over a one hour period and at a rate such that the reaction temperature increased from 21° C. to 29° C. during the course of the addition. At the end of the addition, solid thiourea (0.12 mole, 9.13 grams) is added to the reactor in nine equal portions over the next hour. During this addition, the reaction temperature decreased from 29° C. to 25° C. At the end of the one hour solid thiourea addition, the reaction temperature is increased to 35° C. and held therein for the next four hours. The resulting product solution is poured into iced deionized water (200 grams), then the precipitated resin extracted into chloroform (400 grams). The chloroform extract is added to a separatory funnel and washed with deionized water (400 milliliters). The separated organic layer is washed a second time with deionized water (400 milliliters), recovered and rotary evaporated under vacuum using final conditions of 100° C. and 4 mm Hg for 60 minutes. The product is recovered (120.3 grams) as a light amber colored, transparent liquid (at 24° C.). Thin layer chromatography of a portion of the product on a silica gel plate using a 3/2/2/2 volume mixture of hexane/ethyl acetate/ chloroform/methanol as the eluent followed by visualization via treatment of the plate with 5% phosphomolybdic acid in ethanol then heat, versus the diglycidyl ether of 3,3',5,5'-tetramethyl-4,4'-dihydroxy-alpha-methylstilbene reactant (Rf=0.690) demonstrates that total conversion of the diglycidyl ether to a single product (Rf=0.841) has occurred. Fourier transform infrared spectrophotometric analysis of neat films of the diglycidyl ether of 3,3',5,5'-tetramethyl-4,4'-dihydroxy-alpha-methylstilbene reactant versus the product on NaCl plates demonstrates that total conversion of the epoxide group (920 cm$^{-1}$) to the thiirane group (618 cm$^{-1}$) has occurred.

EXAMPLE 2

A. Synthesis of 4,4'-Dihydroxy-alpha-methylstilbene

Phenol (376.44 grams, 4.0 moles), chloroacetone (192.77 grams, 2.0 moles as chloroacetone) and methylene chloride (300 grams) are added to a one liter glass resin kettle reactor equipped with a chilled water condenser, mechanical stirrer, nitrogen purge (1 liter per minute), thermometer and dry ice-methylene chloride cooling bath and cooled to −10° C. with stirring. The chloroacetone used is a commercial grade containing 96% chloroacetone. Concentrated sulfuric acid (196.16 grams, 2.0 mole) is added dropwise to the stirred solution over a thirty minute period and so as to maintain the reaction temperature between −10° and −11° C. After 150 minutes of post reaction between a −10° to −11° C. temperature range, the viscous, opaque, orange colored oil product is mixed with iced deionized water (500 milliliters). The oil product is separated then washed with a second portion (500 milliliters) of deionized water. After separation, the recovered oil product is added to a 2 liter beaker along with ethanol (250 milliliters) and stirred to provide a solution. Deionized water (250 milliliters) is added to the stirred solution and heating commences. As the temperature of the mixture increases, the stirred mixture begins to clear. Each time clearing is observed, sufficient deionized water is added to induce cloudiness, followed by continuation of the mixing and heating. Once the temperature reaches 70° C., a massive precipitation of white crystalline plates occurs and is followed by immediate coalesence of the precipitated product to an oil. The oil layer is recovered by decantation of the water layer and ethanol (250 milliliters) is added. Deionized water is again added to the stirred solution as heating commences, in an amount sufficient to induce cloudiness each time clearing is observed. Once the temperature reaches 90° C., a massive precipitation of white crystalline plates again occurs. At this time, stirring is stopped and the crystalline slurry is chilled to 5° C. and held therein for 12 hours. The crystalline product is recovered by filtration of the chilled crystalline slurry and combined with deionized water (800 milliliters), then stirred with heating to 100° C. After maintaining the stirred slurry at 100° C. for thirty minutes, the crystalline product is recovered by filtration then dried in a vacuum oven at 100° C. and 5 mm Hg to a constant weight of 251.3 grams. Proton magnetic resonance spectroscopy and infrared spectrophotometric analysis confirms the product structure.

B. Epoxidation of 4,4'-dihydroxy-alpha-methylstilbene 4,4'-Dihydroxy-alpha-methylstilbene (158.38 grams, 1.40 hydroxyl equivalent) from A. above, epichlorohydrin (647.71 grams, 7.00 moles), deionized water (56.32 grams, 8.0 percent by weight of the epichlorohydrin used) and isopropanol (348.77 grams, 35 percent by weight of the epichlorohydrin used) are added to a two liter glass resin kettle reactor equipped with a chilled water condenser, mechanical stirrer, nitrogen purge (1 liter per minute), thermometer and thermostatically controlled infrared heating lamps and heated to 55° C. with stirring under a nitrogen atmosphere. Once the 55° C. reaction temperature is achieved, sodium hydroxide (50.4 grams, 1.26 moles) dissolved in deionized water (201.6 grams) is added dropwise to the reactor over a 45 minute period and so as to maintain reaction temperature between 55° and 58° C. Ten minutes after completion of the aqueous sodium hydroxide addition, the stirring is stopped and the aqueous layer which separated from the reaction mixture is pipetted off and discarded. Stirring is resumed and after a total of twenty minutes following completion of the initial aqueous sodium hydroxide addition, a second solution of sodium hydroxide (22.4 grams, 0.56 mole) dissolved in deionized water (89.6 grams) is added to the reactor over a twenty minute period and so as to maintain the 55° C. reaction temperature. Fifteen minutes after completion of the aqueous sodium hydroxide addition, the recovered reaction mixture is added to a separatory funnel and washed with 750 milliliters of deionized water. The separated organic layer is washed a second time (750 milliliters deionized water), recovered and then rotary evaporated under vacuum for 45 minutes at 110° C. then 30 minutes at 130° C. The product is recovered (227.9 grams) as a off-white, crystalline solid. Recrystallization is completed by dissolving the dry crystalline product in boiling acetone (600 milliliters) followed by chilling to 5° C. and filtering off the white crystalline product after 12 hours. After drying in a vacuum oven at 80° C. and 5 mm Hg to a constant weight, the product is recovered with an epoxide equivalent weight of 182.81.

C. Conversion of the Diglycidyl Ether of 4,4'-dihydroxy-alpha-methylstilbene to the Dithiirane A portion of the diglycidyl ether of 4,4'-dihydroxy-alpha-methylstilbene (63.98 grams, 0.35 epoxide equivalent) from B. above, 1,4-dioxane (175 grams) and methanol (175 grams) are added to a two liter glass resin kettle reactor equipped with a chilled water condenser, nitrogen purge (1 liter per minute), thermometer and thermostatically controlled infrared heating lamps and maintained at 24° C. with stirring under a nitrogen atmosphere. A solution of thiourea (0.336 mole, 25.58 grams) in 1,4-dioxane (175 grams) and methanol (175 grams) is added to the slurry in the reactor over a one hour period during which time the reaction temperature remains at 24° C. At the end of the addition, solid thiourea (0.084 mole, 6.39 grams) is added to the reactor in a single portion and with no effect on the reaction temperature. At the end of the solid thiourea addition, the reaction temperature is increased to 35° C. and held therein for the next two hours. Thin layer chromatographic analysis (conditions used follow in this example) of a chloroform extract of portion of the reaction slurry which has been diluted into deionized water reveales the presence of only the unreacted diglycidyl ether. At this time, the addition of chloroform (600 milliliters) to the reactor followed by reestablishment of the 35° C. reaction temperature is completed to provide a solution. After an additional 17 hours of reaction at 35° C., the product solution is poured into deionized water (one half gallon), then the chloroform product layer is recovered using a separatory funnel and then washed with deionized water (500 milliliters). The separated organic layer is recovered and rotary evaporated under vacuum using final conditions of 100° C. and 4 mm Hg for 60 minutes. The product is recovered (60.5 grams) as a white crystalline solid. Thin layer chromatography of a portion of the product on a silica gel plate using a 4/1 volume mixture of hexane/ethyl acetate followed by visualization via treatment of the plate with 5% phosphomolybdic acid in ethanol then heat, versus the diglycidyl ether of 4,4'-dihydroxy-alpha-methylstilbene reactant (Rf=0.282) demonstrates that total conversion of the diglycidyl ether to a single product (Rf=0.493) has occurred. Fourier transform infrared spectrophotometric analysis of neat films of the diglycidyl ether of 4,4'-dihydroxy-alpha-methylstilbene reactant versus the product on NaCl plates demonstrates that total conversion of the epoxide group (920 cm$^{-1}$) to the thiirane group (617 cm$^{-1}$) has occurred.

EXAMPLE 3

Characterization of the Dithiirane Ether of 4,4'-Dihydroxy-alpha-methylstilbene for Liquid Crystallinity A portion (9.59 milligrams) of the dithiirane ether of 4,4'-dihydroxy-alpha-methylstilbene from Example 2-C is analyzed by differential scanning calorimetry using a heating rate of 20° C. per minute and a temperature range of 30° to 170° C. The results are indicated in Table I.

TABLE I

| Cycle Designation | Observed Transition Temperatures (°C.) midpoint/range | Enthalpy (J/G) | Comments |
|---|---|---|---|
| First heating (30 to 170° C.) | 144/97–158 | 88.8 | single endotherm |
| First cooling (170 to 30° C.) | 86/90–46 | 39.0 | single exotherm |

Analysis of the dithiirane ether via crosspolarized light microscopy is completed using a microscope equipped with a programmable hot stage using a heating rate of 20° C. per minute. The results are indicated in Table II.

TABLE II

| Cycle Designation | Observed Transition Temperatures (°C.) | Comments |
|---|---|---|
| First heating (24 to 145.3° C.) | 137.6 | First fluidity noted, birefringent crystals moving in an isotropic fluid. |
|  | 145.3 | Isotropization completed. |
| First cooling (145.3 to 30° C.) | 105.6 | Birefringent crystalline solid formed. |
| Second heating (30 to 145° C.) | 138.3 | First fluidity noted, birefringent crystals moving in an isotropic fluid. |
|  | 145 | Isotropization completed. |
| Second cooling (145 to 30° C.) | 104.2 | Birefringent crystalline solid formed. |
| Third heating (30 to 144.6° C.) | 138.1 | First fluidity noted, birefringent crystals moving in an isotropic fluid. |
|  | 144.6 | Isotropization completed. |

COMPARATIVE EXPERIMENT A

Characterization of Liquid Crystallinity in the Diglycidyl Ether of 4,4'-Dihydroxy-alpha-methylstilbene A portion (12.78 milligrams) of the diglycidyl ether of 4,4'-dihydroxy-alpha-methylstilbene from Example 2-B is analyzed by differential scanning calorimetry using a heating rate of 10° C. per minute and a temperature range of 30° to 150° C. The results are indicated in Table III.

TABLE III

| Cycle Designation | Observed Transition Temperatures (°C.) midpoint/range | Enthalpy (J/G) | Comments |
|---|---|---|---|
| First heating (30 to 150° C.) | 78/70–87 | 2.3 | single exotherm |
|  | 131/93–144 | 79.5 | single endotherm |
| First cooling (150 to 30° C.) | 96/98–87 | 1.7 | single exotherm |
|  | 55/62–41 | 29.3 | single exotherm |
| Second heating (30 to 150° C.) | 66/48–90 | 27.8 | single exotherm |

TABLE III-continued

| Cycle Designation | Observed Transition Temperatures (°C.) midpoint/range | Enthalpy (J/G) | Comments |
|---|---|---|---|
|  | 129/105–143 | 82.5 | single endotherm |
| Second cooling (150 to 30° C.) | 97/99–88 | 1.3 | single exotherm |
|  | 55/62–41 | 29.2 | single exotherm |

Analysis of the diglycidyl ether via crosspolarized light microscopy is completed using a microscope equipped with a programmable hot stage using a heating rate of 20° C. per minute. The results are indicated in Table IV.

TABLE IV

| Cycle Designation | Observed Transition Temperatures (°C.) | Comments |
|---|---|---|
| First heating (24 to 129° C.) | 30 (30) | Birefringent crystalline solid. |
|  | 125 (126.5) | First fluidity noted. birefringent crystals moving in an isotropic fluid. |
|  | 129 (129) | Isotropization completed. |
| First cooling (129 to 30° C.) | 92 (95.6) | First mobile nematic droplets observed. |
|  | 76 (76.5) | Crystallizes. |
| Second heating (30 to 129° C.) | 123.5 | First fluidity noted, birefringent crystals moving in an isotropic fluid. |
|  | 129 | Isotropization completed. |
| Second cooling (129 to 30° C.) | 90.5 | First mobile nematic droplets observed. |
|  | 67.7 | Crystals start to form in the nematic fluid. |
|  | 59.7 | Fully crystallized. |

The values for observed transition temperatures in parentheses for the first heating and first cooling represent the results of a duplicate microscopic examination. The diglycidyl ether is a monotropic liquid crystal with a nematic texture. The nematic fluid gives opalescence when stirred between the 90° and 76° C. temperatures of the first cooling cycle.

EXAMPLE 4

A. Preparation of a Neat Resin Casting of the Dithiirane Ether of 4,4'-Dihydroxy-alpha-methylstilbene Without a Curing Agent or Catalyst To characterize the self curing behavior of the dithiirane ether of 4,4'-dihydroxy-alpha-methylstilbene prepared in Example 2-C, a sample of this resin is first analyzed by differential scanning calorimetry at a heating rate of 10° C. per minute to 300° C. This analysis shows a cure exotherm for the resin immediately following melt (150° C.) which has a peak temperature of 240° C. For the preparation of a neat resin casting of the dithiirane ether of 4,4'-dihydroxy-alphamethylstilbene, one gram of the resin, contained in an aluminum cup, is placed in a 170° C. oven. In the 170° C. oven, the resin is observed to melt and then gel within 10 minutes. After 1 hour at 170° C., the resin, which has cured to a rubbery, translucent solid, is removed from the oven. For the polymer thus obtained, a high level of birefringence is observed via crosspolarized light microscopy at 70× magnification. The glass transition temperature for this polymer is 34° C. as determined by differential scanning calorimetry. In this differential scanning calorimetry analysis, no additional thermal activity is observed to 175° C. These results are reported in Table V.

B. Preparation of a Neat Resin Casting of the Dithiirane Ether of 4,4'-Dihydroxy-alpha-methylstilbene Without a Curing Agent or Catalyst For the preparation of a neat resin casting of the dithiirane ether of 4,4'-dihydroxy-alpha-methylstilbene, prepared in Example 2-C, one gram of the resin, contained in an aluminum cup, is placed in a 150° C. oven. In the 150° C. oven, the resin is observed to melt and then gel within 15 minutes. After 12 hours at 150° C., the resin, which has cured to an opaque solid, is removed from the oven. For the polymer thus obtained, a high level of birefringence around the edges of the casting is observed via crosspolarized light microscopy at 70× magnification. The glass transition temperature for this polymer is 75° C. as determined by differential scanning calorimetry. In this differential scanning calorimetry analysis, no additional thermal activity is observed to 175° C. These results are reported in Table V.

C. Preparation of a Neat Resin Casting of the Dithiirane Ether of 4,4'-Dihydroxy-alpha-methylstilbene Using 2-Methylimidazole One gram of the dithiirane ether of 4,4'-dihydroxy-alpha-methylstilbene is first added to 25 milliliters of acetone containing 0.001 grams of 2-methylimidazole (0.1 PHR based on the dithiirane ether of 4,4'-dihyroxy-alpha-methylstilbene added). After stirring this solution for 30 minutes, it is allowed to evaporate to dryness at room temperature (22° C.). The solid resin obtained is then ground to a fine powder. This powder is then placed in an aluminum cup. For cure, the aluminum cup containing the resin is placed in a 170° C. oven. After one hour at 170° C., the resin, which has cured to a translucent solid, is removed from the oven. For the polymer thus obtained, a high level of birefringence is observed via crosspolarized light microscopy at 70× magnification. Differential scanning calorimetry analysis of this polymer shows a broad step transition over the temperature range of 88° C. to 190° C. These results are reported in Table V.

D. Preparation of a Neat Resin Casting of a Blend of the Dithiirane Ether of 4,4'-Dihydroxy-alpha-methylstilbene and the Diglycidyl Ether of 4,4'-Isopropylidenediphenol Using 2-Methylimidazole A 20 weight percent solution of 2-methylimidazole in methanol (0.075 grams) is first added to 0.500 grams of the diglycidyl ether of 4,4'-isopropylidenediphenol (epoxide equivalent weight=179.9), contained in an aluminum cup. After mixing the 2-methylimidazole with the diglycidyl ether of 4,4'-isopropylidenediphenol, 0.500 grams of the dithiirane ether of 4,4'-dihydroxy-alphamethylstilbene prepared in Example 2-C is added after grinding this resin to a fine powder. Mixing of these components results in a pasty blend which contains 1.5 PHR 2-methylimidazole based on total resin. For cure, the aluminum cup containing the resin blend is placed in an oven preheated to 125° C. In the 125° C. oven, the resin blend sets to a solid in less than 2 minutes. After 1 hour at 125° C., the oven temperature is raised to 170° C. After 1 hour at 170° C., the resin, which is an opaque solid, is removed from the oven. For the polymer thus obtained, birefringence around the edges of the casting is observed via crosspolarized light microscopy at 70× magnification. The glass transition temperature for this polymer is 155° C. as determined by differential scanning calorimetry. These results are reported in Table VI.

E. Preparation of a Neat Resin Casting of the Dithiirane Ether of 4,4'-Dihydroxy-alpha-methylstilbene Cured with 4,4'-Dihydroxy-alpha-methylstilbene One gram of the dithiirane ether of 4,4'-dihydroxy-alpha-methylstilbene (0.00499 equivalents) prepared in Example 2-C and 0.565 grams of 4,4-dihydroxy-alpha-methylstilbene (0.00499 equivalents) prepared in Example 2-A are added to 25 milliliters of acetone containing 0.0047 grams of tetrabutylphosphonium acetate acetic acid complex. After stirring this solution for 30 minutes, it is allowed to evaporate to dryness at room temperature (22° C.). The solids obtained are then ground to a fine powder and then placed in an aluminum cup. For cure, the aluminum cup containing the resin blend is placed in a 170° C. oven. In the 170° C. oven, the resin blend is observed to melt and then gel within 3 minutes. After 1 hour at 170° C., the resin blend, which has cured to a translucent solid, is removed from the oven. For the polymer thus obtained a high level of birefingence is observed via crosspolarized light microscopy at 70× magnification. The glass transition temperature for this polymer is 66° C. as determined by differential scanning calorimetry. In this differential scanning calorimetry analysis, no additional thermal activity is observed to 175° C.

F. Preparation of a Neat Resin Casting of the Dithiirane Ether of 4,4'-Dihydroxy-alpha-methylstilbene Cured with 4,4'-Dihydroxy-alpha-methylstilbene One gram of the dithiirane ether of 4,4'-dihydroxy-alpha-methylstilbene (0.00499 equivalents) prepared in Example 2-C and 0.282 grams of 4,4'-dihydroxy-alpha-methylstilbene (0.00249 equivalents) are added to 25 milliliters of acetone containing 0.0050 grams of a 1 to 1 equivalence of a tetrabutylphosphonium acetate.acetic acid complex and fluoroboric acid. After stirring this solution for 30 minutes, it is allowed to evaporate to dryness at room temperature (22° C.). The solids obtained are then ground to a fine powder and then placed in an aluminum cup. For cure, the aluminum cup containing the resin blend is placed in a 170° C. oven. In the 170° C. oven, the resin blend is observed to melt and then gel within 3 minutes. After 1 hour at 170° C., the resin blend, which has cured to a semitranslucent solid, is removed from the oven. For the polymer thus obtained, a high level of birefringence is observed via crosspolarized light microscopy at 70× magnification. The glass transition temperature for this polymer is 81° C. as determined by differential scanning calorimetry. In this differential scanning calorimetry analysis, no additional thermal activity is observed to 175° C.

EXAMPLE 5

Preparation of a Neat Resin Casting of the Dithiirane Ether of 3,3',5,5'-Tetramethyl-4,4'-Dihydroxy-alpha-methylstilbene Without a Curing Agent or Catalyst To characterize the self curing behavior of the dithiirane ether of 3,3',5,5'-tetramethyl-4,4'-dihydroxy-alpha-methylstilbene prepared in Example 1-C, a sample of this resin (22.7 milligrams) is first analyzed by differential scanning calorimetry at a heating rate of 10° C. per minute to 300° C. This analysis shows a cure exotherm for the resin which had an onset and peak temperature of 135° C. and 236° C., respectively. dithiirane ether of 3,3',5,5'-tetramethyl-4,4'-dihydroxy-alpha-methylstilbene, 2.31 grams of the resin, contained in an aluminum cup, is placed in a 150° C. oven. In the 150° C. oven, the resin is observed to gel within 20 minutes. After 12 hours at 150° C., the resin, which has cured to a semitranslucent solid, is removed from the oven. For the polymer thus obtained, dispersed regions having a crystalline appearance are observed via crosspoplarized light microscopy at 70× magnification. The glass transition temperature for this polymer is 78° C. as determined by differential scanning calorimetry. In this differential scanning calorimetry analysis no additional thermal activity is observed to 175° C.

COMPARATIVE EXPERIMENT B

Preparation of a Neat Resin Casting of the Diglycidyl Ether of 4,4'-Isopropylidenediphenol Using 2-Methylimidazole

1. Diglycidyl Ether of 4,4'-Isopropylidenediphenol Containing 1.5 PHR 2-Methylimidazole A 20 weight percent solution of 2-methylimidazole in methanol (0.075 grams) is added to 1.000 grams of the diglycidyl ether of 4,4'-isopropylidenediphenol (epoxide equivalent weight=179.9), contained in an aluminum cup. After mixing the 2-methylimidazole with the resin, it is placed in a 125° C. oven. In the 125° C. oven, the resin is observed to gel within 5 minutes. After 1 hour at 125° C., the oven temperature is increased to 170° C. After 1 hour at 170° C., the resin which had cured to a translucent solid, is removed from the oven. For the polymer thus obtained, no birefringence is observed via crosspolarized light microscopy at 70× magnification. The glass transition temperature for this polymer is 116° C. as determined by differential scanning calorimetry. In this differential scanning calorimetry analysis, no additional thermal activity is observed to 200° C. These results are reported in Table VI.

2. Diglycidyl Ether of 4,4'-Isopropylidenediphenol Containing 0.1 PHR 2-Methylimidazole For further comparative purposes, a 4.0 weight percent solution of 2-methylimidazole in methanol (0.025 grams) is added to 1.000 grams of the diglycidyl ether of 4,4'-isopropylidenediphenol (epoxide equivalent weight=179.9), contained in an aluminum cup. After mixing the 2-methylimidazole with the resin, it is placed in a 170° C. oven. After 1 hour at 170° C., the resin is removed from the oven. On cooling to room temperature (22° C.), the resin remained a liquid, indicating little, if any, cure has occurred. These results are reported in Table V.

TABLE V

Preparation of Neat Resin Castings

| | Example 4-A | Example 4-B | Example 4-C | Comparative Experiment B-2* |
|---|---|---|---|---|
| Curing Catalyst | None | None | 2-Methylimidazole (0.1 PHR) | 2-Methylimidazole (0.1 PHR) |
| Cure Scheule | 1 Hour @ 170° C. | 12 Hours @ 170° C. | 1 Hour @ 170° C. | 1 Hour @ 170° C. |
| Glass Transition Temperature of Cured Resin by DSC, °C. | 34 | 75 | 88 (Apparent) | No Cure |
| Morphology of Cured Resin (70X Magnification, Crosspolarized Light Source) | Birefringent | Birefringent | Birefringent | — |

*Not an example of the present invention.

TABLE VI

Preparation of Neat Resin Castings

| | Example 4-D | Comparative Experiment B-1* |
|---|---|---|
| Curing Catalyst | 2-Methylimidazole (1.5 PHR) | 2-Methylimidazole (1.5 PHR) |
| Cure Schedule | 1 Hour @ 125° C.+ 1 Hour @ 170° C. | 1 Hour @ 125° C.+ 1 Hour @ 170° C. |
| Glass Transition Temperature of Cured Resin by DSC, °C. | 155 | 116 |
| Morphology of Cured Resin (70X Magnification, Crosspolarized Light Source) | Birefringent | Non-Birefringent |

*Not an example of the present invention.

EXAMPLE 6

A. Preparation of 4,4'-Dihydroxybenzophenone Oxime from 4,4'-Dihydroxybenzophenone 4,4'-Dihydroxybenzophenone (100.0 grams, 0.467 mole) is added to ethanol (300 millimeters) in a one liter Erlenmeyer flask and stirred. Once the 4,4'-dihydroxybenzophenone is in solution, a solution of hydroxylamine hydrochloride (48.6 grams, 0.699 mole) and sodium acetate (57.4 grams, 0.70 mole) in water (70 millimeters) is added to the flask, followed by additional ethanol (100 milliliters). The stirred mixture is heated on a hot plate to a gentle reflux (75° C.). After four hours at reflux, the stirred solution is cooled to room temperature and then filtered. The resultant filter cake is washed with ethanol (100 milliliters), then the total filtrant obtained (600.4 grams) concentrated to a weight of 219.2 grams by evaporation of part of the ethanol. The concentrated solution and deionized water (600 milliliters) are placed in a one liter Erlenmeyer flask and stirred. The addition of the deionized water induced the formation of a white precipitate. After thirty minutes of stirring, the slurry is filtered and the recovered white powder is dried in a vacuum oven to a constant weight of 98.22 grams. Fourier transform infrared spectrophotometric analysis of a potassium bromide pellet of the product confirms the product structure for 4,4'-dihydroxybenzophenone oxime (hydroxyl O—H stretching at 3400 cm$^{-1}$, aromatic C—O stretching at 1235 cm$^{-1}$, aromatic ring C—C stretching at 1607 and 1513 cm$^{-1}$). Differential scanning calorimetry of a portion of the product heated at 10° C. per minute under nitrogen flowing at 35 cubic centimeters per minute reveals a melting point endotherm at 155° C. followed by an exotherm (rearrangement of 4,4'-dihydroxybenzophenone oxime to 4,4'-dihydroxybenzanilide) at 155° to 188° C. Following this exotherm, a melting point endotherm for the rearrangement product is observed at 269° C. High pressure liquid chromatographic analysis of a portion of the 4,4'-dihydroxybenzophenone product indicates a purity of 97.8%.

B. Preparation of 4,4'-Dihydroxybenzanilide from 4,4'-Dihydroxybenzophenone Oxime 4,4'-Dihydroxybenzophenone oxime (66.0 grams, 0.288 mole) from Experiment A-1 and acetic acid (330 milliliters) are added to a 500 milliliter round bottom flask equipped with a stirrer, nitrogen purge, water cooled condenser and thermostatically controlled heating mantle. p-Toluenesulfonic acid catalyst (1.85 grams, 0.027 mole) is added to the stirred reaction mixture, and heating commences. After heating for two hours at 83° C., a precipitate forms. The reaction mixture is then stirred for an additional two hours at 87° C. and then diluted with deionized water (25 milliliters). Thirty minutes later, the contents of the reaction flask are transferred to a one liter Erlenmeyer flask and stirred. Immediately following this transfer, additional deionized water (400 milliliters) is added. The mixture is stirred for an additional 45 minutes, then filtered. The filter cake obtained is washed with deionized water (800 milliliters), then recovered and dried in a vacuum oven to a constant weight of 54.2 grams of light beige colored product. Fourier transform infrared spectrophotometric analysis of a potassium bromide pellet of the product confirms the product structure for 4,4'-dihydroxybenzanilide (secondary amide N—H stretching absorbance (solid state) at 3322 cm$^{-1}$, aromatic C—O stretching at 1251 cm$^{-1}$, aromatic ring C—C stretching at 1609 and 1514 cm$^{-1}$, secondary amide carbonyl stretching (solid state) at 1646 cm$^{-1}$). Differential scanning calorimetry of a portion of the product heated at 10° C. per minute under nitrogen flowing at 35 cubic centimeters per minute reveals a sharp melting point endotherm at 273° C.

C. Epoxidation of 4,4'-Dihydroxybenzanilide 4,4'-Dihydroxybenzanilide (99.6 grams, 0.869 hydroxyl equivalent) prepared using the method of Experiment A-2, epichlorohydrin (804.57 grams, 8.70 moles), deionized water (69.96 grams, 8.0 percent by weight of the epichlorohydrin used) and isopropanol (433.23 grams, 35 percent by weight of the epichlorohydrin used) are added to a reactor and heated to 65° C. with stirring under a nitrogen atmosphere. Once the 65° C. reaction temperature is achieved, sodium hydroxide (31.31 grams, 0.78 mole) dissolved in deionized water (125.25 grams) is added dropwise to the reactor over a one hour period and so as to maintain reaction temperature at 65° C. Fifteen minutes after completion of the aqueous sodium hydroxide addition, the stirring is stopped and the aqueous layer which separates from the reaction mixture is pipetted off and discarded. Stirring is resumed and after a total of twenty minutes following completion of the initial aqueous sodium hydroxide addition, a second solution of sodium hydroxide (13.92 grams, 0.35 mole) dissolved in deionized water (55.66 grams) is added to the reactor over a thirty minute period and so as to maintain the 65° C. reaction temperature. Fifteen minutes after completion of the aqueous sodium hydroxide addition, the recovered reaction mixture is added to a separatory funnel the aqueous layer which separated is removed and discarded. As the remaining organic layer cooled, sufficient methylene chloride is added to maintain a solution in the separatory funnel. The organic layer is then washed four times with deionized water comprising approximately one half the total volume of the organic layer. The recovered organic layer is rotary evaporated under vacuum for 45 minutes at 125° C. The product is recovered (142.03 grams) as an off-white, crystalline solid with an epoxide equivalent weight of 178.0 and a melting point of 180°-185° C. Fourier transform infrared spectrophotometric analysis of a potassium bromide pellet of the product reveals the presence of secondary amide N—H stretching (solid state) absorbance at 3283 cm$^{-1}$, secondary amide carbonyl stretching (solid state) absorbance at 1643 cm$^{-1}$, out-of-plane C-H bending vibration absorbance at 832 cm$^{-1}$ due to the paradisubstituted aromatic rings and epoxide ring absorbances at 912 and 835 cm$^{-1}$.

D. Conversion of the Diglycidyl Ether of 4,4'-Dihydroxybenzanilide to the Dithiirane A portion of the diglycidyl ether of 4,4'-dihydroxybenzanilide (4.45 grams, 0.025 epoxide equivalent) from Experiment A-3, 1,4-dioxane (100 grams) and methanol (100 grams) are added to a reactor and maintained at 50° C. with stirring under a nitrogen atmosphere. A solution of thiourea (0.03 mole, 2.28 grams) in 1,4-dioxane (24 grams) and methanol (24 grams) is added to the solution in the reactor while maintaining the 50° C. temperature. High pressure liquid chromatographic analysis of a portion of the reaction product after 30 hours reveals that full conversion of the diglycidyl ether to a single product has occurred. At this time, the solution is added to stirred deionized water (800 milliliters) followed by filtration five minutes later to recover the precipitated product. The resultant dried filter cake is washed with deionized water (25 milliliters) then dried in a vacuum oven at 50° C. and 1 mm Hg to a constant weight (4.72 grams) of white crystalline powder. Fourier transform infrared spectrophotometric analysis reveals the presence of secondary amide N—H stretching (solid state) absorbance at 3329 cm$^{-1}$, secondary amide carbonyl stretching absorbance at 1643 cm$^{-1}$, out-of-plane C—H bending vibration absorbance at 826 cm$^{-1}$ due to the paradisubstituted aromatic rings and thiirane ring absorbance at 620 cm$^{-1}$ concurrent with complete disappearance of the epoxide ring absorbances at 912 and 835 cm$^{-1}$.

E. Characterization of the Dithiirane Ether of 4,4'-Dihydroxybenzanilide for Liquid Crystallinity and for Glass Transition Temperature of the Homopolymerization Product A portion (9.1 milligrams) of the dithiirane ether of 4,4'-dihydroxybenzanilide from Experiment A-4 is analyzed by differential scanning calorimetry using a heating rate of 10° C. per minute and a temperature range of 30° to 250° C. under a stream of nitrogen flowing at 35 cubic centimeters per minute. The following results are obtained:

| Observed Transition Temperatures, °C. | | | Enthalpy | |
|---|---|---|---|---|
| Onset | Midpoint | End | J/g | Comments |
| 154 | 169 | 176 | 30.9 | Single Exotherm |
| 176 | 184 | 218 | 109 | Single Exotherm |

The 176° C. temperature marking the end of the first exotherm and the onset of the second exotherm is below the baseline observed before either of the exothermic events and may thus represent endothermic behavior associated with melting. A second scan differential scanning calorimetry analysis is completed using the aforementioned conditions and reveals a glass transition temperature of 162° C. The cured dithiirane ether recovered from the second scan differential scanning calorimetry analysis is a fused light tan colored solid. Examination of this cured dithiirane ether via crosspolarized light microscopy reveals alack of birefringence.

Analysis of a portion of the dithiirane ether via crosslinked light microscopy is completed using a microscope equipped with a programmable hot stage using a heating rate of 10° C. per minute. The following results are obtained:

| Observed Transition Temperatures, °C. | Comments |
|---|---|
| 170 | First softening noted as sample is compressed between the coverslip and slide. |
| 174 | Birefringent opalescent fluid composed of fine dispersed crystals. |
| 179 | Thermosets to an opalescent solid with grainy birefringent texture due to fine crystals. |

F. Characterization of the Diglycidyl Ether of 4,4'-Dihydroxybenzanilide by Differential Scanning Calorimetry A portion (11.7 milligrams) of the diglycidyl ether of 4,4'-dihydroxybenzanilide from Experiment A-3 is analyzed by differential scanning calorimetry using a heating rate of 10° C. per minute and a temperature range of 30° to 250° C. udner a stream of nitrogen flowing at 35 cubic centimeters per minute. The following results are obtained:

| Observed Transition Temperatures, °C. | | | Enthalpy | |
|---|---|---|---|---|
| Onset | Midpoint | End | J/g | Comments |
| 141 | 163 | 172 | * | Single Endotherm |
| 172 | 185 | 194 | * | Single Endotherm |

*Collective enthalpy for the two endotherms = 120.0 J/g.

An exotherm with an onset temperature at 225° C. is additionally observed. A second scan differential scanning calorimetry analysis is completed using the aforementioned conditions and reveals a glass transition temperature of 62.3° C., followed by a pair of endotherms with an onset temperature of 113° C., midpoints of 132° C. and 140° C., respectively, and an endpoint temperature of 147° C. A collective enthalpy for the two endotherms of 2.09 J/g is obtained. An exotherm with an onset temperature at 221° C. is additionally observed.

EXAMPLE 7

A. Epoxidation of 4,4'-Stilbenedicarboxylic Acid 4,4'-Stilbenedicarboxylic acid (32.93 grams, 0.2455 —COOH equivalent), epichlorohydrin (1135.9 grams, 12.28 mole) and tetrabutylammonium chloride (0.329 gram, 1.0% wt. of the diacid reactant used) are added to a two liter glass round bottom reactor and heated to 80° C. with magnetically driven stirring under a nitrogen atmosphere flowing at a rate of one liter per minute. After five hours at the 80° C. reaction temperature, infrared spectrophotometric analysis demonstrated complete conversion of the carboxylic acid groups (acid carbonyl absorbance at 1682 cm$^{-1}$) to ester groups (ester carbonyl absorbance at 1716 cm$^{-1}$) concurrent with the formation of a hazy, light brown colored solution. At this time, a water separator is interspersed between the reactor and the chilled (−2.5° C.) glycol condenser and an addition funnel containing sodium hydroxide (11.05 grams, 0.276 mole) dissolved in deionized water (13.50 grams, 55% wt. of the solution) and a vacuum line are added to the reactor. The nitrogen purge is shut off simultaneous with initiation of the vacuum. The vacuum and reaction temperature are equilibrated at 83 mm Hg and 60° C., respectively, and such that a vigorous reflux is maintained with continuous return of dry epichlorohydrin from the water separator to the reactor. After equilibration, dropwise addition of the aqueous sodium hydroxide commences accompanied by a gradual reduction in vacuum and reaction temperature. After 53 minutes, addition of the aqueous sodium hydroxide is complete and vacuum and reaction temperature are at 65 mm Hg and 54° C., respectively. After an additional 2 hours at the 65 mm Hg vacuum and 54° C. reaction temperature, heating ceases and the product slurry is cooled to 50° C. The recovered slurry is filtered under a nitrogen atmosphere and the resultant light amber colored solution rotary evaporated under a vacuum (5 mm Hg final conditions) at 90° C. for 30 minutes. The white powder product recovered from the rotary evaporation is dissolved in methylene chloride (1000 milliliters), added to a separatory funnel and washed with deionized water. The recovered organic layer is dried over anhydrous sodium sulfate, then filtered and rotary evaporated under a vacuum (1 mm Hg final conditions) at 80° C. for 60 minutes.

The product is recovered (39.45 grams) as a white crystalline powder. Titration of a portion of the product reveals an epoxide equivalent weight of 198.41. Fourier transform infrared spectrophotometric analysis of a potassium bromide pellet of the product reveals the presence of ester carbonyl stretching absorbance at 1716 cm$^{-1}$, out-of-plane C—H bending vibration at 859 cm$^{-1}$ due to the paradisubstituted aromatic rings, an out-of-plane C—H deformation at 985 cm$^{-1}$ (972 and 959 cm$^{-1}$ shoulders) due to the trans substituted ethylene group and epoxide ring absorbances at 906 and 852 cm$^{-1}$ (overlaps with the 859 cm$^{-1}$ absorbance).

B. Conversion of the Diglycidyl Ester of 4,4'-Stilbenedicarboxylic Acid to the Dithiirane A portion of the diglycidyl ester of 4,4'-stilbenedicarboxylic acid (4.96 grams, 0.025 epoxide equivalent) from Experiment B-1 above, 1,4-dioxane (100 grams) and methanol (100 grams) are added to a reactor and maintained at 50° C. with stirring under a nitrogen atmosphere. A solution of thiourea (0.03 mole, 2.28 grams) in 1,4-dioxane (50 grams) and methanol (50 grams) is added to the solution in the reactor while maintaining the 50° C. temperature. High pressure liquid chromatographic analysis of a portion of the reaction product after 26.8 hours reveals that full conversion of the diglycidyl ester to a single product has occurred. At this time, the solution is added to stirred deionized water (1000 milliliters) followed five minutes later by addition to a separatory funnel and extraction with three portions (400 milliliters) of ethyl acetate. The combined extracts are dried over anhydrous sodium sulfate then filtered. The filtrate is rotary evaporated at 70° C. and 1 mm Hg to a constant weight (5.11 grams) of white crystalline powder. Fourier transform infrared spectrophotometric analysis revealed the presence of ester carbonyl stretching absorbance at 1716 cm$^{-1}$, out-of-plane C—H bending vibration absorbance at 859 cm$^{-1}$ due to the para-disubstituted aromatic rings, an out-of-plane C—H deformation absorbance at 985 cm$^{-1}$ (959 cm$^{-1}$ shoulder) due to the trans substituted ethylene group and thiirane ring absorbance at 613 cm$^{-1}$ concurrent with complete disappearance of the epoxide ring absorbances at 906 and 852 cm$^{-1}$.

Characterization of the Dithiirane Ester of 4,4'-Stilbenedicarboxylic Acid for Liquid Crystallinity and for Glass Transition Temperature of the Homopolymerization Product A portion (11.7 milligrams) of the dithiirane ester of 4,4'-stilbenedicarboxylic acid from Experiment B-2 is analyzed by differential scanning calorimetry using a heating rate of 10° C. per minute and a temperature range of 30° to 250° C. under a stream of nitrogen flowing at 35 cubic centimeters per minute. A single endotherm results with a gradual onset at 84° C. and a minimum at 138° C. This endotherm is immediately followed by an exotherm with a maximum at 170° C. and an end at 201° C.

A second portion (12.7 milligrams) of the dithiirane ester is cured in the differential scanning calorimeter using the following conditions under a nitrogen atmosphere: heat at 10° C. per minute from 30° C. to 135° C. and hold therein for 20 minutes, heat at 10° C. per minute from 135° C. to 175° C. and hold therein for 20 minutes, heat at 10° C. per minute from 175° C. to 200° C. and hold therein for 20 minutes, heat at 10° C. per minute from 200° C. to 220° C. and hold therein for 20 minutes. A second scan differential scanning calorimetry analysis is completed using the conditions given in Experiment A-5 and reveals a glass transition temperature of 163.9° C. The cured dithiirane ester recovered from the second scan differential scanning calorimetry analysis is a fused brown colored solid. Examination of this cured dithiirane ester via crosspolarized light microscopy reveals a lack of birefringence.

Analysis of a portion of the dithiirane ester via crosspolarized light microscopy is completed using a microscope equipped with a programmable hot stage using a heating rate of 10° C. per minute. The following results are obtained:

| Observed Transition Temperatures, °C. | Comments |
|---|---|
| 126 | First fluidity noted. |
| 131 | Isotropic fluid containing birefringent fine dispersed crystals, opalescent. |
| 155 | Fluid starting to clear, still opalescent. |
| 165 | Viscous fluid, opalescent, grainy texture due to fine dispersed crystals. |
| 175 | Highly viscous fluid. When sheared, gives clumps of birefringent crystals aggregated to domains, opalescent. |
| 180 | Thermosets to an opalescent solid with retention of the birefringent crystalline domains. |

D. Characterization of the Diglycidyl Ester of 4,4'-Stilbenedicarboxylic Acid by Differential Scanning Calorimetry A portion (11.6 milligrams) of the diglycidyl ester of 4,4'-stilbenedicarboxylic acid from Experiment B-2 is analyzed by differential scanning calorimetry using a heating rate of 10° C. per minute and a temperature range of 30° to 250° C. under a stream of nitrogen flowing at 35 cubic centimeters per minute. The following results are obtained:

| Observed Transition Temperatures, °C. | | | Enthalpy | |
|---|---|---|---|---|
| Onset | Midpoint | End | J/g | Comments |
| 110.5 | 137 | 145 | 78.5 | Single Endotherm |

A second scan differential scanning calorimetry analysis is completed using the aforementioned conditions and results in the same endotherm as observed in the initial analysis.

What is claimed is:

1. A blend comprising (A) at least one thiirane resin containing an average of more than one thiirane group and at least one rodlike mesogenic moiety per molecule; and (B) an epoxy resin containing an average of more than one vicinal epoxide group per molecule.

2. A blend of claim 1 wherein said thiirane resin is a resin represented by the following Formulas I, II or III

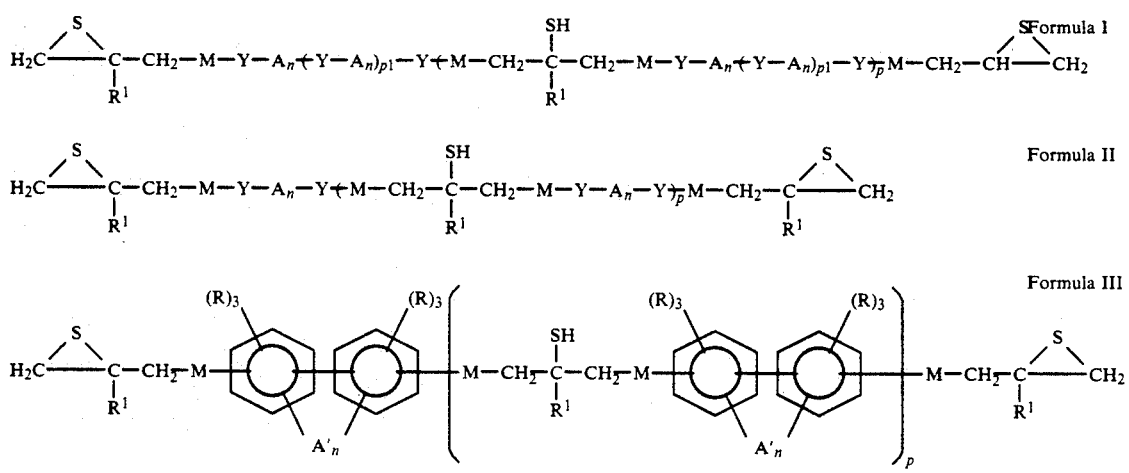

where each Y is independently

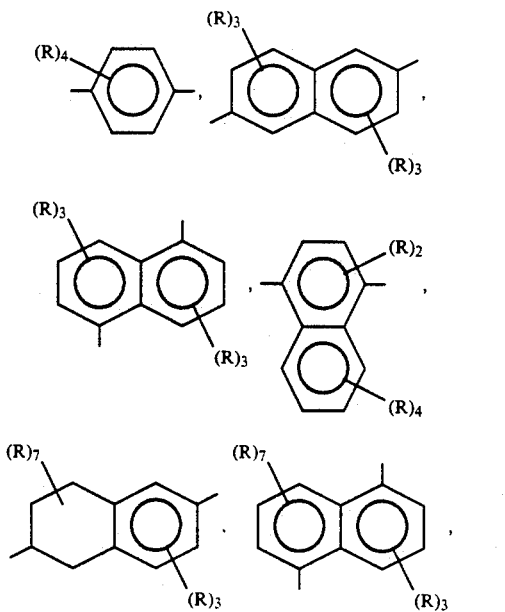

-continued

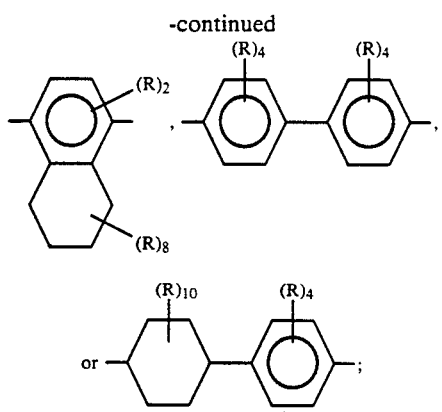

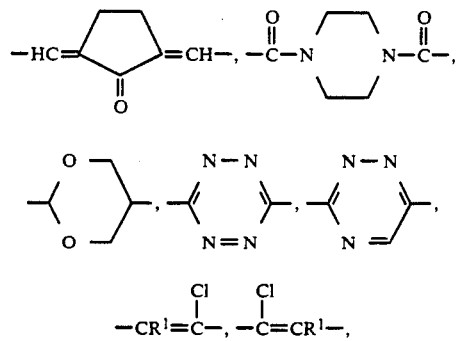

each M is independently (a) —O—, —S—, or —CO—O— wehre the single bonded oxygen atom attached to the carbon atom of —CO—O— is attached to the

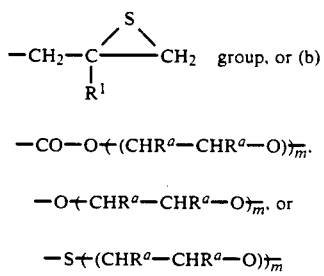

group, or (b)

—CO—O—(CHR$^a$—CHR$^a$—O)$_{\overline{m}}$,

—O—(CHR$^a$—CHR$^a$—O)$_{\overline{m}}$, or

—S—(CHR$^a$—CHR$^a$—O)$_{\overline{m}}$ where a single bonded oxygen atom is attached to the

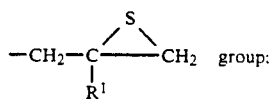

group;

each R$^a$ is independently hydrogen or an alkyl or haloalkyl group containing from 1 to about 2 carbon atoms with the proviso that only one R$^a$ group can be a haloalkyl group; m has a value from 1 to about 100; each A is independently a direct single bond, —CR$^1$=CR$^1$—, —C≡C—, —N=N—, —CR$^1$=N—, —O—CO—, —NR$^1$—CO—, —CR$^1$=N—N=CR$^1$—, —CR$^1$=CR$^1$—CO—, —N=CR$^1$—, —CO—O—, —CO—NR$^1$—, —CO—CR$^1$=CR$^1$—, —CO—O—N=CR$^1$—, —CR$^1$=N—O—OC—, —CO—NR$^1$—NR$^1$—OC—, —CR$^1$=CR$^1$—O—OC—, —CO—O—CR$^1$=CR$^1$—, —O—OC—CR$^1$=CR$^1$—, —CR$^1$=CR$^1$—CO—O—, —CHR$^1$—O—CO—CR$^1$=CR$^1$—, —CR$^1$=CR$^1$—CO—O—CHR$^1$, —CHR$^1$—CO—O—CR$^1$=CR$^1$—, —CR$^1$=CR$^1$—O—CO—CHR$^1$—, —CO—S—, —S—OC—, —CH$_2$—CH$_2$—CO—O—, —O—O—C—CH$_2$—CH$_2$—, —C≡C—C≡C—, —CR$^1$=CR$^1$—CR$^1$=CR$^1$—,

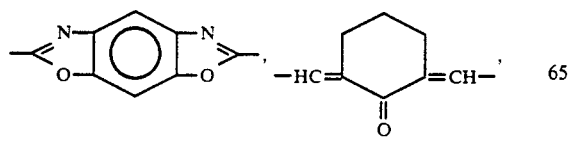

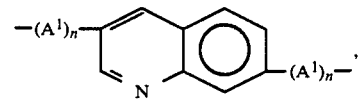

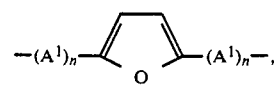

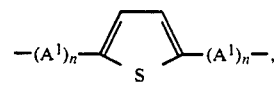

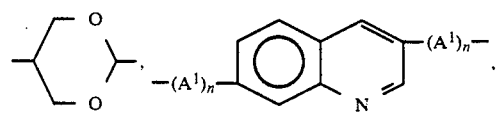

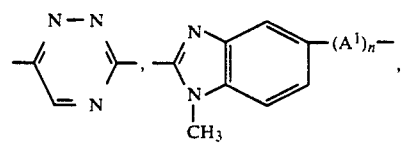

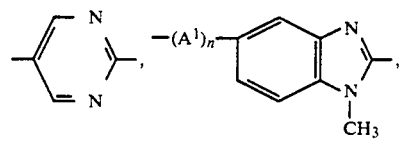

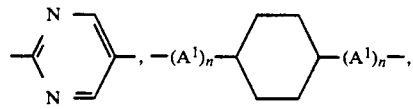

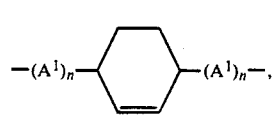

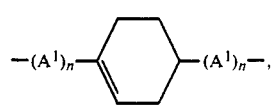

-continued

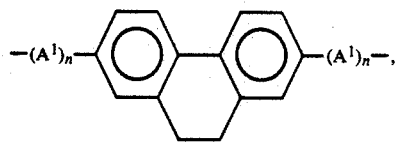
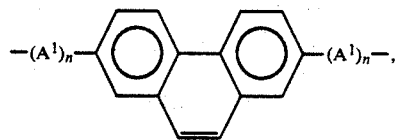
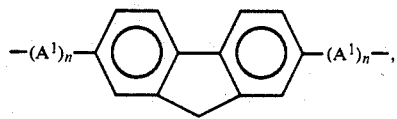
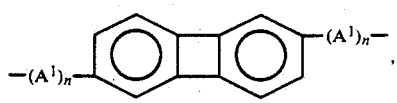
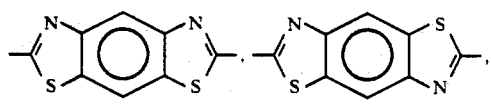
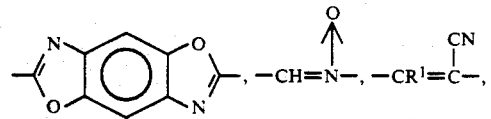
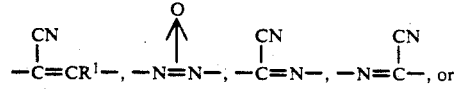

-continued

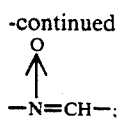

each A' is independently a divalent hydrocarbyl group having from 1 to about 10 carbon atoms; each $A^1$ is independently a

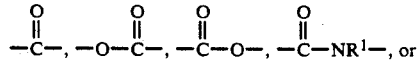

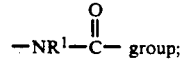 group;

each R is independently hydrogen or a hydrocarbyl or hydrocarbyloxy group having from 1 to about 10 carbon atoms, a halogen atom, a nitro group, a nitrile group, or a —CO—$R^1$ group each $R^1$ is independently hydrogen or a hydrocarbyl group having 1 to about 3 carbon atoms; n has a value of zero or one; p has a value from zero to about 30; and $p^1$ has a value from 1 to about 30;.

3. A blend of claim 2 wherein said thiirane resin is a dithiirane ether of 4,4'-dihydroxybiphenyl, 4,4'-dihydroxystilbene, 4'-dihydroxy-diphenylacetylene, 4,4'-dihydroxydiphenylazomethine, 4,4'-dihydroxyazobenzene, 4,4'-dihydroxyazoxybenzene, 4,4'-bis((4-hydroxy)phenoxy)diphenyl, 3,3',5,5'-tetramethyl-4,4'-dihydroxydiphenyl, 3,3',5,5'-tetrachloro-4,4'-dihydroxydiphenyl, 2,2',6,6'-tetramethyl-4,4'-dihydroxydiphenyl, bis (4-hydroxyphenyl)terephthalate, N,N'-bis(4-hydroxyphenyl)terephthalamide, 4-hydroxyphenyl-4-hydroxybenzoate, 4,4'-dihydroxybenzanilide, N-methyl4,4'-dihydroxybenzanilide, 4,4'-dihydroxy-alpha-methylstilbene, 4,4'-dihydroxychalcone, 4,4'-dihydroxy-alpha-cyanostilbene, 2,2'-dimethyl-4,4'-dihydroxyazoxybenzene, 4,4'-dihydroxy-a,a'-dimethylstilbene, 4,4''-dihydroxybiphenylbenzoate, 4,4'-dihydroxy-a,a'-diethylstilbene, bis(4'-hydroxyphenyl)-1,4-benzenediimine, bis(4'-hydroxybiphenyl)terephthalate, or a dithiirane ether of a dihydric phenol represented by one of the following formulae:

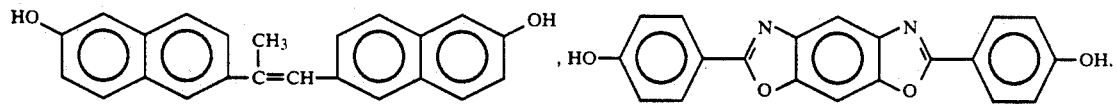

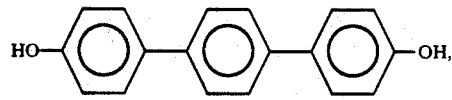

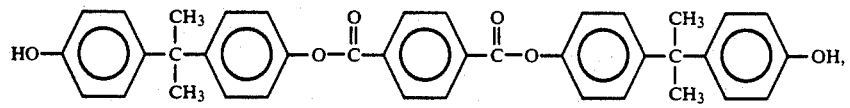

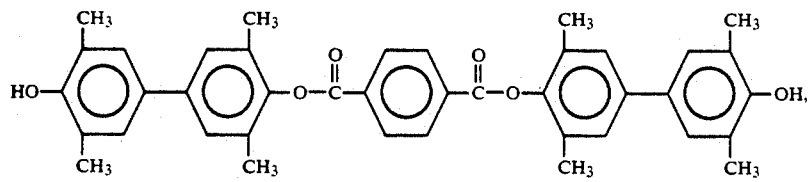

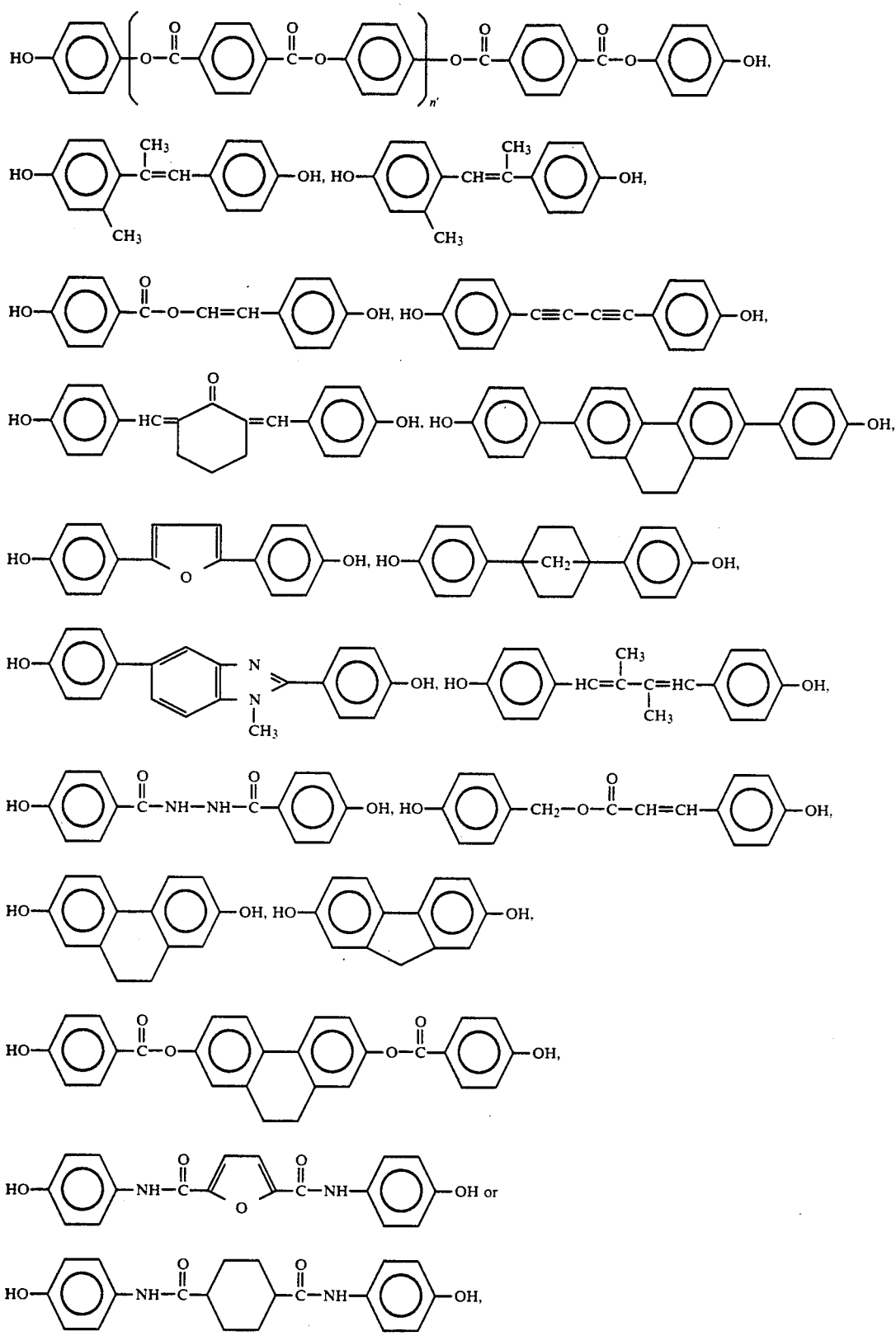

wherein n' has a value of from 1 to about 10 and a dithiirane resin resulting from advancing said dithiirane ether with a dicarboxylic acid or an aromatic dihydroxyl compound; or a mixture of said dithiirane resins.

4. A blend of claim 2 wherein said thiirane resin is the dithiirane of the diglycidyl ether of: 4,4'-dihydroxy-alpha-methylstilbene, 3,3'5,5'-tetramethyl-4,4'-dihydroxy-alpha-methylstilbene, or 4,4'-dihydroxybenzanilide, or the dithiirane of the diglycidyl ester of 4,4'-stilbenedicarboxylic acid or any combination thereof.

5. A blend of claim 1, 2, 3 or 4 wherein said thiirane resin is oriented.

6. A blend claim 5 wherein said orientation is conducted by means of an electric or magnetic field or by drawing or shear forces.

* * * * *